(12) United States Patent
Lehr et al.

(10) Patent No.: US 8,242,055 B2
(45) Date of Patent: *Aug. 14, 2012

(54) HERBICIDALLY AND INSECTICIDALLY ACTIVE PHENYL-SUBSTITUTED PYRIDAZINONES

(75) Inventors: Stefan Lehr, Liederbach (DE); Thomas Schenke, Bergisch Gladbach (DE); Christopher Hugh Rosinger, Hofheim (DE); Reiner Fischer, Monheim (DE); Isolde Häuser-Hahn, Leverkusen (DE); Dieter Feucht, Eschborn (DE); Jan Dittgen, Frankfurt (DE); Pierre Cristau, Köln (DE); Oliver Gaertzen, Köln (DE); Stefan Herrmann, Langenfeld (DE); Olga Malsam, Rösrath (DE); Eva-Maria Franken, Limonest (FR)

(73) Assignee: Bayer Cropscience AG, Monheim (DE)

( * ) Notice: Subject to any disclaimer, the term of this patent is extended or adjusted under 35 U.S.C. 154(b) by 135 days.

This patent is subject to a terminal disclaimer.

(21) Appl. No.: 12/638,180

(22) Filed: Dec. 15, 2009

(65) Prior Publication Data

US 2010/0184602 A1 Jul. 22, 2010

(30) Foreign Application Priority Data

Dec. 19, 2008 (EP) .................................... 08022104

(51) Int. Cl.
*A01N 43/58* (2006.01)
*A61K 31/50* (2006.01)
*C07D 237/00* (2006.01)

(52) U.S. Cl. ........................ 504/236; 514/247; 544/224
(58) Field of Classification Search .................. 544/224; 514/247; 504/236
See application file for complete search history.

(56) References Cited

U.S. PATENT DOCUMENTS

2010/0032020 A1  2/2010  Labegorre et al.

FOREIGN PATENT DOCUMENTS

| EP | 2041491 | 4/2009 |
| GB | 2293169 | 3/1996 |
| JP | 11152273 | * 6/1999 |
| WO | 2007014054 | 2/2007 |
| WO | 2007119434 | 10/2007 |
| WO | WO 2007/119434 | * 10/2007 |
| WO | 2008/003907 | 1/2008 |
| WO | 2009/035145 | 3/2009 |
| WO | 2009035150 | 3/2009 |
| WO | 2009/086041 | 7/2009 |

OTHER PUBLICATIONS

Stevenson et al., J. Het. Chem. 43, 427 (2005).*
Co-Pending U.S. Appl. No. 12/638,105.*
International Search Report of PCT/EP2009/008906, dated May 27, 2010 (3 pages).
Maes et al., "Synthesis of 4-aryl-5-hydroxy- and 5-aryl-4-hydroxypyridazin-3(2H)-ones and their use in the preparation of 4,5-diarylpyridazin-3(2H)-ones and hitherto unknown isochromeno[3,4-d]pyridazinediones," 58, Tetrahedron, pp. 9713-9721 (2002), Elsevier Science Ltd.
Stevenson,Thomas M. et al, "Application of Cross-Coupling and Metalation Chemistry of 3(2H)-Pyridazinones to Fungicide and Herbicide Discovery", Journal of Heterocyclic Chemistry, Heterocorporation. Provo, US, Bd. 42, Nr. 3, Apr. 1, 2005, Seiten 427-435, XP002442886.
Kametani, T, et al, "Synthesis of 2-Nitro-4, 5-Dimethoxyphenylfatty Acid Hydrazide and Its Related Compounds and Their Anti-Cancer Activity", Yakugaku Zasshi—Journal of the Pharmaceutical Society of Japan, JP Bd. 83, Nr. 9, Jan. 1, 1963, Seiten 851-855, XP008064239.
Kametani, T, et al, "The Reaction of (2-Bromo-4,5-Dimethoxyphenyl)-Acetic Acid Hydrazide With Various Carbonyl Compounds and Their Anti-Cancer Activity", Yakugaku Zasshi—Journal of the Pharmaceutical Society of Japan, JP Bd. 83, Jan. 1, 1963, Seiten 844-847, XP008064238.
European Search Report of Application No. EP08022104, dated Apr. 1, 2009.

* cited by examiner

*Primary Examiner* — Paul V. Ward
(74) *Attorney, Agent, or Firm* — Baker, Donelson, Bearman, Caldwell & Berkowitz, PC

(57) ABSTRACT

The invention describes phenyl-substituted pyridazinones of the formula (I) as herbicides and insecticides.

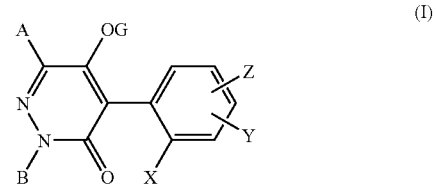

In this formula (I), A, B, G, X, Y and Z are radicals such as hydrogen, organic radicals such as alkyl, and other radicals such as halogen, nitro and cyano.

15 Claims, No Drawings

HERBICIDALLY AND INSECTICIDALLY ACTIVE PHENYL-SUBSTITUTED PYRIDAZINONES

CROSS REFERENCE TO RELATED APPLICATIONS

This application claims priority to European Application 08022104.7 filed Dec. 19, 2008, the content of which is incorporated herein by reference in its entirety.

BACKGROUND OF THE INVENTION

1. Field of the Invention
Herbicidally and Insecticidally Active Phenyl-Substituted Pyridazinones The invention relates to the technical field of the crop protection agents, in particular that of the herbicides for the selective control of broad-leaved weed and weed grasses in crops of useful plants.

It specifically relates to aryl-substituted pyridazinone derivatives, processes for their preparation and their use as herbicides and insecticides.

2. Description of Related Art

Various publications describe substituted 4-phenylpyridazinones having herbicidal properties. 2-Methyl-4-phenylpyridazinones are known from Stevenson et. al, *J. Het. Chem.*, (2005), 427 ff. WO2007/119434 A1 describes 4-phenylpyridazinones which carry an alkyl radical in the 2-position of the phenyl ring. WO2009/035150 A2 discloses 4-phenylpyridazinones which carry an alkyl or alkoxy radical in the 2-position of the phenyl ring and are optionally substituted at the other positions by halogen atoms or other radicals.

However, the compounds known from these publications frequently have insufficient herbicidal activity. Accordingly, it is an object of the present invention to provide alternative herbicidally active compounds.

SUMMARY OF THE INVENTION

It has been found that 4-phenylpyridazinones whose phenyl ring carries certain substituents are particularly suitable as herbicides.

The present invention provides 4-phenylpyridazinones of the formula (I) or salts thereof

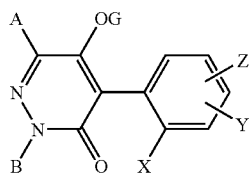

(I)

in which
A and B are in each case independently of one another hydrogen or $(C_1-C_6)$-alkyl;
G is hydrogen, $C(=O)R^1$, $C(=L)MR^2$, $SO_2R^3$, $P(=L)R^4R^5$, $C(=L)NR^6R^7$ or E;
E is a metal ion equivalent or an ammonium ion;
L is oxygen or sulfur;
M is oxygen or sulfur;
$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, each of which is substituted by n halogen atoms,
a fully saturated 3- to 6-membered ring consisting of 3 to 5 carbon atoms and 1 to 3 heteroatoms from the group consisting of oxygen, sulfur and nitrogen which is substituted by n radicals from the group consisting of halogen, $(C_1-C_4)$-alkyl and $(C_1-C_4)$-alkoxy,
$(C_3-C_6)$-cycloalkyl, phenyl, phenyl-$(C_1-C_4)$-alkyl, heteroaryl, phenoxy-$(C_1-C_4)$-alkyl or heteroaryloxy-$(C_1-C_4)$-alkyl substituted by n radicals from the group consisting of halogen, $(C_1-C_4)$-alkyl and $(C_1-C_4)$-alkoxy;
$R^2$ is $(C_1-C_6)$-alkyl, $(C_2-C_6)$-alkenyl, $(C_1-C_4)$-alkoxy-$(C_1-C_6)$-alkyl or di-$(C_1-C_4)$-alkoxy-$(C_1-C_6)$-alkyl, each of which is substituted by n halogen atoms,
or is $(C_3-C_6)$-cycloalkyl, phenyl or benzyl, each of which is substituted by n radicals from the group consisting of halogen, $(C_1-C_4)$-alkyl and $(C_1-C_4)$-alkoxy;
$R^3$, $R^4$ and $R^5$ are each independently of one another $(C_1-C_6)$-alkyl which is substituted by n halogen atoms, $(C_1-C_4)$-alkoxy, N—$(C_1-C_6)$-alkylamino, N,N-di-$(C_1-C_6)$-alkylamino, $(C_1-C_4)$-alkylthio, $(C_2-C_4)$-alkenyl or $(C_3-C_6)$-cycloalkylthio,
or phenyl, benzyl, phenoxy or phenylthio which is substituted by n radicals from the group consisting of halogen, $(C_1-C_4)$-alkyl and $(C_1-C_4)$-alkoxy;
$R^6$ and $R^7$ are each independently of one another hydrogen, $(C_1-C_6)$-alkyl which is substituted by n halogen atoms, $(C_3-C_6)$-cycloalkyl, $(C_2-C_6)$-alkenyl, $(C_1-C_6)$-alkoxy or $(C_1-C_4)$-alkoxy-$(C_1-C_6)$-alkyl,
phenyl or benzyl, each of which is substituted by n radicals from the group consisting of halogen, $(C_1-C_4)$-alkyl and $(C_1-C_4)$-alkoxy;
or $R^6$ and $R^7$ together with the nitrogen atom to which they are attached form a 3- to 6-membered ring which contains 2 to 5 carbon atoms and 0 or 1 oxygen or sulfur atoms;
m is 1, 2 or 3;
n is 0, 1, 2 or 3;
X is halogen, cyano, $(C_3-C_6)$-cycloalkyl, nitro or is $(C_1-C_6)$-alkyl or $(C_1-C_6)$-alkoxy each of which is substituted by m halogen atoms substituted or phenyl substituted by n halogen atoms;
Y and Z are each independently of one another hydrogen, halogen, cyano, nitro, $(C_3-C_6)$-cycloalkyl or are $(C_1-C_6)$-alkyl, $(C_1-C_6)$-alkoxy or phenyl, each of which is substituted by n halogen atoms,
with the proviso that neither Y nor Z is a $(C_1-C_6)$-alkyl or $(C_1-C_6)$-alkoxy radical located in position 6 if n is 0.

DETAILED DESCRIPTION OF A PREFERRED EMBODIMENT

If G and/or B are hydrogen, the compounds of the formula (I) according to the invention can, depending on external conditions such as pH, solvent and temperature, be present in various tautomeric structures which are all embraced by the general formula (I):

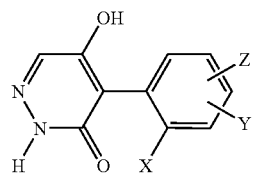 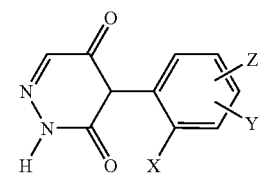

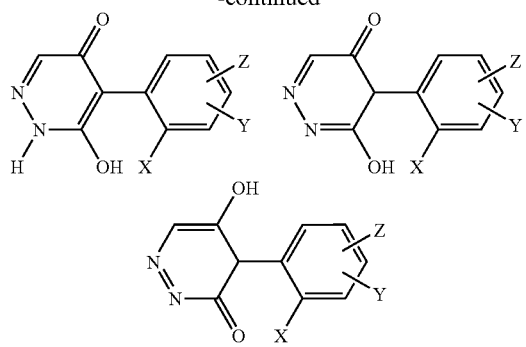

In all the structures below, the substituents have, unless defined otherwise, the same meaning as given above for the compounds of the formula (I).

Compounds of the formula (I) according to the invention in which G is hydrogen can be prepared, for example, according to the method given in Scheme 1 by a base-induced condensation reaction of compounds of the formula (II). Here, $R^9$ is ($C_1$-$C_6$)-alkyl, in particular methyl or ethyl.

Scheme 1

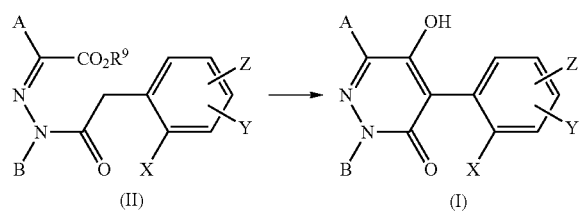

The compounds of the formula (II) can be prepared, for example, according to the method given in Scheme 1a by reaction of hydrazonocarboxylic acid derivatives with phenylacetic acid derivatives. Here, U is a leaving group introduced by reagents for activating carbonxylic acids, such as carbonyldiimidazole, carbonyldiimides (such as, for example, dicyclohexylcarbodiimide), phosphorylating agents (such as, for example, $POCl_3$, BOP—Cl), halogenating agents such as, for example, thionyl chloride, oxalyl chloride, phosgene or chloroformic esters. Such methods are also known to the person skilled in the art from WO2007/119434, BCS07-3099 and the documents cited therein.

Scheme 1a

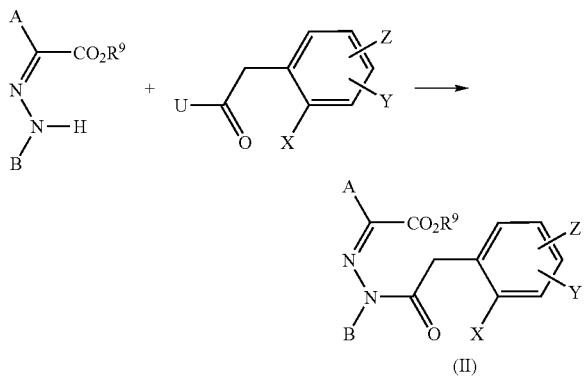

Compounds of the formula (II) can also be prepared, for example, according to the method shown in Scheme 1b, by the reaction, known to the person skilled in the art from Zh. Obs. Khim. 1992, 62, 2262, of hydrazides (IIa) with ketocarboxylic acids of the formula A-CO—$CO_2R^9$.

Scheme 1b

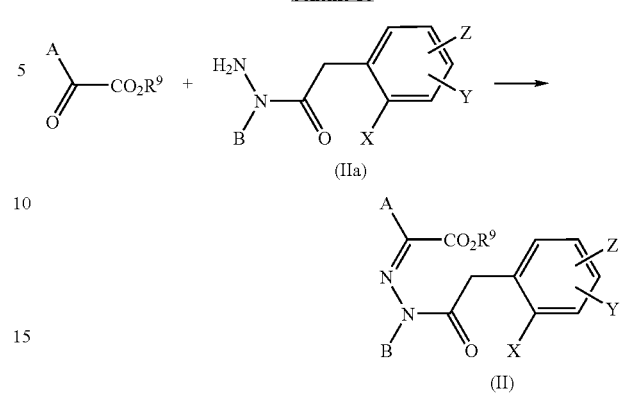

The hydrazides of the formula (IIa) shown in Scheme 1b can be prepared, for example, by reacting hydrazines of the formula B—NH—$NH_2$ with the phenylacetic acid derivatives shown in Schema 1a according to the method described in J. Org. Chem. 1980, 45, 3673. The hydrazides shown in Scheme 1a can be prepared from the ketocarboxylic acids A-CO—$CO_2R^9$ shown in Scheme 1b, which are known per se, for example according to the methods described in J. Med. Chem. 1985 (28), 1436.

The free phenylacetic acids required for preparing the phenylacetic acid derivatives shown in Schema 1a, i.e. those in which U is hydroxyl, are known or can be prepared by processes which are known per se, for example from WO 2005/075401, WO 2001/96277, WO 1996/35664 and WO 1996/25395.

However, certain phenylacetic acid derivatives can also be prepared using acetic ester enolates in the presence of palladium catalysts, for example formed from a palladium source (for example $Pd_2(dba)_3$ or $Pd(Oac)_2$) and a ligand (for example $(t-Bu)_3P$, iMes*HCl or 2'-(N,N-dimethylamino)-2-(dicyclohexylphosphanyl)biphenyl) (WO 2005/048710, J. Am. Chem. Soc 2002. 124, 12557, J. Am. Chem. Soc 2003. 125, 11176 or J. Am. Chem. Soc. 2001, 123, 799). In addition, certain substituted aryl halides can be converted under copper catalysis into the corresponding substituted malonic esters (for example described in Org. Lett. 2002, 2, 269, WO 2004/108727), which can be converted by known methods into phenylacetic acids.

Compounds of the formula (I) according to the invention in which G is hydrogen can also be prepared, for example, according to the method given in Scheme 2 by reacting compounds of the formula (I) in which G is alkyl, preferably methyl, with strong mineral bases such as sodium hydroxide or potassium hydroxide, or in concentrated mineral acids such as hydrobromic acid.

Scheme 2

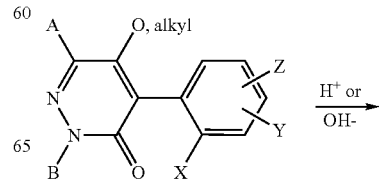

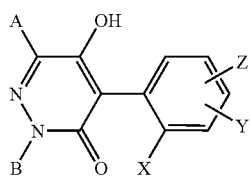

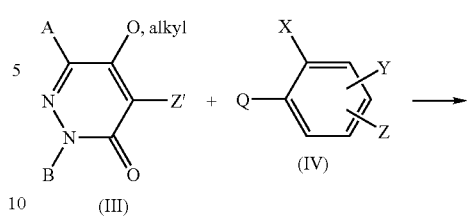

Scheme 3

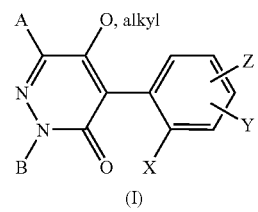

Compounds of the formula (I) according to the invention in which G is C(=O)R¹ can also be prepared, for example, by reactions known to the person skilled in the art of compounds of the formula (I) in which G is hydrogen with carbonyl halides of the formula Hal-CO—R¹ or with carboxylic anhydrides of the formula R¹—CO—O—CO—R¹

Compounds of the formula (I) according to the invention in which G is C(=L)MR² can also be prepared, for example, by reactions known to the person skilled in the art of compounds of the formula (I) in which G is hydrogen with a) chloroformic esters or chloroformic thioesters of the formula R²-M-COOR¹ or b) with chloroformyl halides or chloroformyl thiohalides.

Compounds of the formula (I) according to the invention in which G is $SO_2R^3$ can also be prepared, for example, by reactions known to the person skilled in the art of compounds of the formula (I) in which G is hydrogen with sulfonyl chlorides of the formula R³—$SO_2$—Cl.

Compounds of the formula (I) according to the invention in which G is P(=L)R⁴R⁵ can also be prepared, for example, by reactions known to the person skilled in the art of compounds of the formula (I) in which G is hydrogen with phosphoryl chlorides of the formula Hal-P(=L)R⁴R⁵.

Compounds of the formula (I) according to the invention in which G is E can also be prepared, for example, by reactions known to the person skilled in the art of compounds of the formula (I) in which G is hydrogen with metal compounds of the formula Me(OR¹⁰)$_t$ or with amines. Here, Me is a mono- or divalent metal ion, preferably an alkali or alkaline earth metal such as lithium, sodium, potassium, magnesium or calcium. The index t is 1 or 2. An ammonium ion is the group $NH_4^+$ or $R^{13}R^{14}R^{15}R^{16}N^+$ in which $R^{13}$, $R^{14}$, $R^{15}$ and $R^{16}$ independently of one another are preferably ($C_1$-$C_6$)-alkyl or benzyl.

Compounds of the formula (I) according to the invention in which G is C(=L)NR⁶R⁷ can also be prepared, for example, by reactions known to the person skilled in the art of compounds of the formula (I) in which G is hydrogen with isocyanates or isothiocyanates of the formula R⁶—N=C=L or with carbamoyl chlorides or thiocarbamoyl chlorides of the formula R⁶R⁷N—C(=L)Cl.

Compounds of the formula (I) according to the invention in which G is alkyl, preferably methyl, can also be prepared, for example, according to Scheme 3 by reactions known to the person skilled in the art of compounds of the formula (III) with compounds of the formula (IV). Here, Z' is bromine or iodine and Q is a trialkyltin group, a magnesium halide group or, preferably, a boronic acid or an ester thereof. These reactions are usually carried out in the presence of a catalyst (for example a Pd salt or a Pd complex) and in the presence of a base (for example sodium carbonate, potassium phosphate).

Depending on the nature of the substituents defined above, the compounds of the formula (I) have acidic or basic properties and may be also to form salts, if appropriate also inner salts or adducts, with inorganic or organic acids or bases or with metal ions. If the compounds of the formula (I) carry amino groups, alkylamino groups or other groups which induced basic properties, these compounds may be reacted with acids to salts, or they are directly obtained as salts in the synthesis. Examples of inorganic acids are hydrohalic acids such as hydrofluoric acid, hydrochloric acid, hydrobromic acid and hydroiodic acid, sulfuric acid, phosphoric acid and nitric acid, and acidic salts such as $NaHSO_4$ and $KHSO_4$.

Suitable organic acids are, for example, formic acid, carbonic acid and alkanoic acids such as acetic acid, trifluoroacetic acid, trichloroacetic acid and propionic acid and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals such as phenyl and naphthyl which carry one or two sulfonic acid groups), alkylphosphonic acids (phosphonic acids having straight-chain or branched alkyl radicals having 1 to 20 carbon atoms), arylphosphonic acids or—diphosphonic acids (aromatic radicals such as phenyl and naphthyl which carry one or two phosphonic acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid, etc. Suitable metal ions are in particular the ions of the elements of the second main group, in particular calcium and magnesium, the third and fourth main group, in particular aluminum, tin and lead, and also of the first to eighth transition group, in particular chromium, manganese, iron, cobalt, nickel, copper, zinc and others. Particular preference is given to the metal ions of the elements of the fourth period. Here, the metals may be present in the different valencies that they can assume. If the compounds of the formula (I) carry hydroxyl groups, carboxyl groups or other groups which induce acidic properties, these compounds can be reacted with bases to salts.

Suitable bases are, for example, hydroxides, carbonates, bicarbonates of the alkali and alkaline earth metals, in particular those of sodium, potassium, magnesium and calcium, furthermore ammonia, primary, secondary and tertiary amins having ($C_1$-$C_4$)-alkyl groups, mono-, di- and trialkanolamines of ($C_1$-$C_4$)-alkanols, choline and also chlorocholine.

Halogen is fluorine, chlorine, bromine and iodine.

A metal ion equivalent is a metal ion having a positive charge, such as $Na^+$, $K^+$, $(Mg^{2+})_{1/2}$, $(Ca^{2+})_{1/2}$, $MgH^+$, $CaH^+$, $(Al^{3+})_{1/3}$ $(Fe^{2+})_{1/2}$ or $(Fe^{3+})_{1/3}$.

Alkyl is a saturated straight-chain or branched hydrocarbon radical having 1 to 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methyl-propyl.

Haloalkyl is a straight-chain or branched alkyl group having 1 to 8 carbon atoms (as mentioned above), where some or all of the hydrogen atoms in this group may be replaced by halogen atoms, for example $C_1$-$C_2$-haloalkyl such as chloromethyl, bromomethyl, dichloromethyl, trichloromethyl, fluoromethyl, difluoromethyl, trifluoro-methyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkenyl is an unsaturated straight-chain or branched hydrocarbon radical having 2 to 8 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkoxy is a saturated straight-chain or branched alkoxy radical having 1 to 8 carbon atoms, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethyl-propoxy, 1-ethyl-1-methylpropoxy and 1-ethyl-2-methylpropoxy;

Haloalkoxy is a straight-chain or branched alkoxy group having 1 to 8 carbon atoms (as mentioned above), where some or all of the hydrogen atoms in this group may be replaced by halogen atoms as mentioned above, for example $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chlor-2,2-difluoroethoxy, 2,2-dichloro-2-fluoroethoxy, 2,2,2-trichloroethoxy, pentafluoroethoxy and 1,1,1-trifluoroprop-2-oxy.

Alkylthio is a saturated straight-chain or branched alkylthio radical having 1 to 8 carbon atoms, for example $C_1$-$C_6$-alkylthio such as methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-di-methylpropylthio, 1-ethylpropylthio, hexylthio, 1,1-dimethylpropylthio, 1,2-di-methylpropylthio, 1-methylpentylthio, 2-methylpentylthio, 3-methylpentylthio, 4-methylpentylthio, 1,1-dimethylbutylthio, 1,2-dimethylbutylthio, 1,3-dimethyl-butylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Haloalkylthio is a straight-chain or branched alkylthio group having 1 to 8 carbon atoms (as mentioned above), where some or all of the hydrogen atoms in this group may be replaced by halogen atoms as mentioned above, for example $C_1$-$C_2$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-di-fluoroethylthio, 2,2-dichloro-2-fluoroethylthio, 2,2,2-trichloroethylthio, pentafluoroethylthio and 1,1,1-trifluoroprop-2-ylthio.

Heteroaryl is 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-1-yl, 1,2,4-triazol-3-yl, 1,2,4-triazol-4-yl, 1,2,4-triazol-5-yl, 1,2,3-triazol-1-yl, 1,2,3-triazol-2-yl, 1,2,3-triazol-4-yl, tetrazol-1-yl, tetrazol-2-yl, tetrazol-5-yl, indol-1-yl, indol-2-yl, indol-3-yl, isoindol-1-yl, isoindol-2-yl, benzofur-2-yl, benzothiophen-2-yl, benzofur-3-yl, benzothiophen-3-yl, benzoxazol-2-yl, benzothiazol-2-yl, benzimidazol-2-yl, indazol-1-yl, indazol-2-yl, indazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl or 1,2,4-triazin-6-yl. This heteroaryl is in each case unsubstituted or mono- or polysubstituted by identical or different radicals selected from the group consisting of fluorine, chlorine, bromine, iodine, cyano, hydroxyl, mercapto, amino, methyl, ethyl, n-propyl, isopropyl, n-butyl, isobutyl, sec-butyl, tert-butyl, cyclopropyl, 1-chlorocyclopropyl, vinyl, ethynyl, methoxy, ethoxy, isopropoxy, methylthio, ethylthio, trifluoromethylthio, chlorodifluoromethyl, dichlorofluoromethyl, chlorofluoromethyl, chloromethyl, dichloromethyl, trichloromethyl, fluoromethyl, difluoromethyl, trifluoromethyl, 2,2,2-trifluorethyl, trifluoromethoxy, trifluoromethylthio, 2,2,2-trifluoroethoxy, 2,2-dichloro-2-fluoroethyl, 2,2-difluoro-2-chloroethyl, 2-chloro-2-fluoroethyl, 2,2,2-trichloroethyl, 2,2,2-trifluoroethyl, 2-fluoroethyl, 2,2-difluoroethyl, 2-methoxyethoxy, acetyl, propionyl, methoxycarbonyl, ethoxycarbonyl, N-methylamino, N,N-dimethylamino, N-ethylamino, N,N-diethylamino, aminocarbonyl, methylaminocarbonyl, dimethylaminocarbonyl, dimethylcarbamoylamino, methoxycarbonylamino, methoxycarbonyloxy, ethoxycarbonylamino, ethoxycarbonyloxy, methylsulfamoyl, dimethylsulfamoyl, phenyl or phenoxy.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, their preparation and use and compositions comprising them. However, hereinbelow, for the sake of simplicity, compounds of the formula (I) are always referred to, although this is meant to include both the pure compounds and, if appropriate, mixtures having varying proportions of isomeric compounds.

If a group is polysubstituted by radicals, this is to be understood as meaning that this group is substituted by one or more identical or different radicals from the radicals mentioned.

Preference is given to compounds of the general formulae (I-a), (I-b), (I-c), (I-d), (I-e), (I-f) and (I-g)

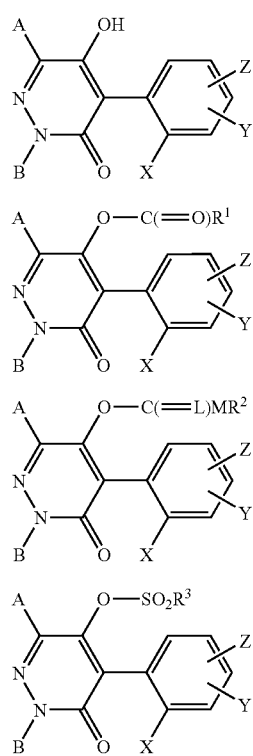

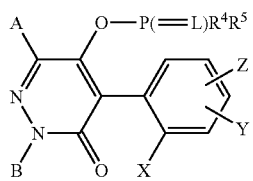

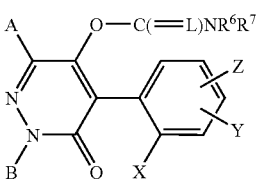

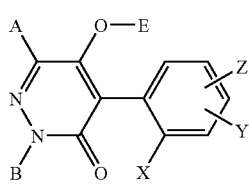

Preference is also given to compounds of the general formula (I) in which
A is hydrogen or $(C_1-C_6)$-alkyl;
B is hydrogen or $(C_1-C_6)$-alkyl;
G is hydrogen, $C(=O)R^1$, $C(=L)MR^2$, $SO_2R^3$, $P(=L)R^4R^5$, $C(=L)NR^6R^7$, or E;
E is $Na^+$, $K^+$, $(Mg)_{1/2}$, $(Ca^{2+})_{1/2}$, $R^{13}R^{14}R^{15}R^{16}N^+$ or $NH_4^+$;
$R^{13}$, $R^{14}$, $R^{15}$ and $R^{16}$ are independently of one another $(C_1-C_6)$-alkyl or benzyl;
L is oxygen;
M is oxygen;
$R^1$ is $(C_1-C_6)$-alkyl which is substituted by n halogen atoms or is $(C_3-C_6)$-cycloalkyl, phenyl or phenyl-$(C_1-C_4)$-alkyl, each of which is substituted by n radicals from the group consisting of halogen, $(C_1-C_4)$-alkyl and $(C_1-C_4)$-alkoxy;
$R^2$ is $(C_1-C_6)$-alkyl which is substituted by n halogen atoms or is $(C_3-C_6)$-cycloalkyl, phenyl or benzyl, each of which is substituted by n radicals from the group consisting of halogen, $(C_1-C_4)$-alkyl and $(C_1-C_4)$-alkoxy;
$R^3$, $R^4$ and $R^5$ are each independently of one another $(C_1-C_6)$-alkyl which is substituted by n halogen atoms or are phenyl or benzyl which are substituted by n radicals from the group consisting of halogen, $(C_1-C_4)$-alkyl and $(C_1-C_4)$-alkoxy;
$R^6$ and $R^7$ are each independently of one another hydrogen, $(C_1-C_6)$-alkyl which is substituted by n halogen atoms or phenyl or benzyl which are substituted by n radicals from the group consisting of halogen, $(C_1-C_4)$-alkyl and $(C_1-C_4)$-alkoxy;
m is 0, 1, 2 or 3;
n is 0, 1, 2, 3, with the proviso that m and n are not 0;
X is halogen, cyano, $(C_3-C_6)$-cycloalkyl, nitro or is $(C_1-C_6)$-alkyl or $(C_1-C_6)$-alkoxy, each of which is substituted by m halogen atoms;
Y and Z are in each case independently of one another hydrogen, halogen, cyano, nitro, $(C_3-C_6)$-cycloalkyl or are $(C_1-C_6)$-alkyl, $(C_1-C_6)$-alkoxy or phenyl, each of which is substituted by n halogen atoms.

Particular preference is given to compounds of the general formula (I) in which
A is hydrogen, methyl, ethyl, isobutyl;
B is hydrogen, methyl, ethyl, isobutyl, tert-butyl;
G is hydrogen, $C(=O)R^1$, $C(=L)MR^2$, $SO_2R^3$, $P(=L)R^4R^5$, $C(=L)NR^6R^7$ or E;

E is $Na^+$, $K^+$, $(Mg^{2+})_{1/2}$, $(Ca^{2+})_{1/2}$, $(CH_3)_4N^+$ or $NH_4^+$;
L is oxygen;
M is oxygen;
$R^1$ is $(C_1-C_6)$-alkyl or $(C_3-C_6)$-cycloalkyl;
$R^2$ is $(C_1-C_6)$-alkyl, $(C_3-C_6)$-cycloalkyl or benzyl;
$R^3$, $R^4$ and $R^5$ are each independently of one another $(C_1-C_6)$-alkyl, phenyl or benzyl;
$R^6$ and $R^7$ are each independently of one another hydrogen, $(C_1-C_6)$-alkyl, phenyl or benzyl;
m is 1, 2 or 3;
n is 0, 1, 2 or 3;
and
X is fluorine, bromine, chlorine, iodine, cyano, nitro, trifluoromethyl, trifluoromethoxy or cyclopropyl;
Y is hydrogen, fluorine, bromine, chlorine, iodine, methyl, ethyl, methoxy, ethoxy, trifluoromethyl, trifluoromethoxy or cyclopropyl;
Z is hydrogen, fluorine, bromine, chlorine, iodine, methyl, ethyl, methoxy, ethoxy, trifluoromethyl, trifluoromethoxy, cyclopropyl, chlorophenyl or fluorophenyl.

Very particular preference is given to the compounds of the general formula (I) listed in Tables 1 to 25 which can be obtained analogously to the methods mentioned here.

The abbreviations used are defined below:

| | | |
|---|---|---|
| Bz = benzyl | c-Pr = cyclopropyl | Et = ethyl |
| i-Bu = isobutyl | t-Bu = tertiary butyl | i-Pr = isopropyl |
| Me = methyl | Ph = phenyl | |

TABLE 1

Compounds of the general formula (I) according to the invention in which G is hydrogen and A and B are each methyl.

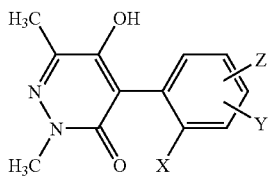

| No. | X | Y | Z |
|---|---|---|---|
| 1 | F | H | H |
| 2 | Cl | H | H |
| 3 | Br | H | H |
| 4 | I | H | H |
| 5 | $CF_3$ | H | H |
| 6 | CN | H | H |
| 7 | $NO_2$ | H | H |
| 8 | $OCF_3$ | H | H |
| 9 | H | 3-$CF_3$ | H |
| 10 | H | 3-Me | H |
| 11 | H | 3-F | H |
| 12 | H | 3-Cl | H |
| 13 | H | 3-CN | H |
| 14 | H | 3-BrI | H |
| 15 | H | 3-I | H |
| 16 | H | 3-$NO_2$ | H |
| 17 | H | 3-$OCF_3$ | H |
| 18 | H | 3-OMe | H |
| 19 | H | 3-$OEt_3$ | H |
| 20 | H | 4-$CF_3$ | H |
| 21 | H | 4-Me | H |
| 22 | H | 4-F | H |
| 23 | H | 4-Cl | H |
| 24 | H | 4-CN | H |
| 25 | H | 4-Br | H |

TABLE 1-continued

Compounds of the general formula (I) according to the invention in which G is hydrogen and A and B are each methyl.

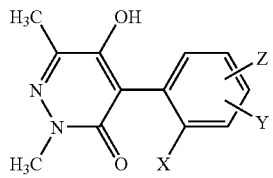

| No. | X | Y | Z |
|---|---|---|---|
| 26 | H | 4-I | H |
| 27 | H | 4-$NO_2$ | H |
| 28 | H | 4-$OCF_3$ | H |
| 29 | H | 4-OMe | H |
| 30 | H | 4-OEt | H |
| 31 | Cl | 4-Cl | H |
| 32 | H | 3-Cl | 4-Cl |
| 33 | Br | 4-Cl | H |
| 34 | Cl | H | 6-Cl |
| 35 | Cl | H | 6-F |
| 36 | F | H | 6-Fl |
| 37 | Cl | 4-Cl | 6-Cl |
| 38 | Br | 4-Me | 6-Br |
| 39 | Cl | 4-Me | 6-Cl |
| 40 | I | H | 4-Me |
| 41 | I | 6-Cl | 4-Me |
| 42 | c-Pr | 4H | H |
| 43 | c-Pr | 4-Me | H |
| 44 | c-Pr | 4-Me | 6-Cl |
| 45 | Cl | 6-F | 3-Me |
| 46 | F | 6-F | 3-F |
| 47 | F | 6-F | 3-OEt |
| 48 | F | H | 5-Cl |
| 49 | H | 3-$CF_3$ | 5-$CF_3$ |
| 50 | $OCF_3$ | 4-Me | H |
| 51 | $OCF_3$ | 5-Me | H |
| 52 | Br | 4-$OCF_3$ | 6-Cl |
| 53 | Br | 4-$OCF_3$ | 6-Br |
| 54 | Cl | 4-$OCF_3$ | 6-Cl |
| 55 | $OCF_3$ | 6-Cl | 4-Br |
| 56 | $OCF_3$ | 6-Cl | 4-Me |
| 57 | Cl | 5-$OCF_3$ | H |
| 58 | Br | 5-$OCF_3$ | H |
| 59 | Cl | 6-$CF_3$ | H |
| 60 | Cl | 3-Cl | 6-$CF_3$ |
| 61 | Cl | 3-F | 6-F |
| 62 | Cl | 4-Cl | 6-c-Pr |
| 63 | Cl | 3-Cl | H |
| 64 | Br | 4-Br | 6-$OCF_3$ |
| 65 | Br | 4-Cl | 6-$OCF_3$ |
| 68 | Cl | 4-Br | 6-$CF_3$ |
| 69 | Br | 4-Cl | 6-$CF_3$ |
| 70 | $CF_3$ | 5-$CF_3$ | H |
| 71 | F | 3-F | H |
| 72 | Cl | 4-Cl | 6-c-Pr |
| 73 | F | 3-Me | 6-F |
| 74 | | | |

Table 2: Compounds of the general formula (I) according to the invention in which G is hydrogen, A is hydrogen and B is ethyl and X, Y and Z each have the meanings given in Table 1.

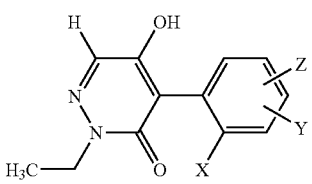

Table 3: Compounds of the general formula (I) according to the invention in which G is hydrogen, A is hydrogen and B is n-propyl and X, Y and Z each have the meanings given in Table 1.

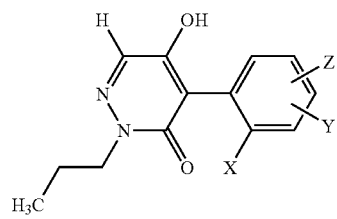

Table 4: Compounds of the general formula (I) according to the invention in which G is hydrogen, A is hydrogen and B is isopropyl and X, Y and Z each have the meanings given in Table 1.

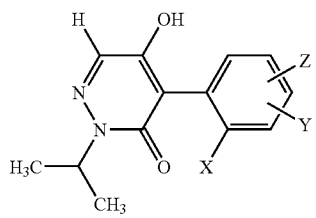

Table 5: Compounds of the general formula (I) according to the invention in which G is hydrogen, and A is methyl and B is methyl and X, Y and Z each have the meanings given in Table 1.

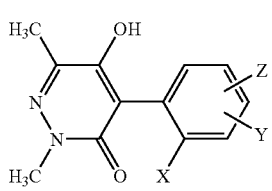

Table 6: Compounds of the general formula (I) according to the invention in which G is hydrogen, A is methyl and B is ethyl and X, Y and Z each have the meanings given in Table 1.

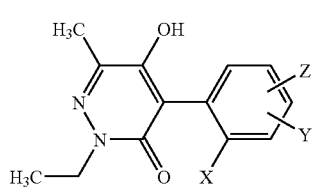

Table 7: Compounds of the general formula (I) according to the invention in which G is hydrogen, A is methyl and B is n-propyl and X, Y and Z each have the meanings given in Table 1.

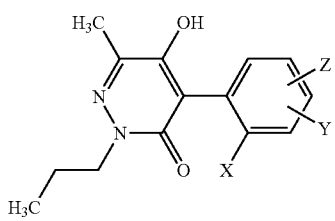

Table 8: Compounds of the general formula (I) according to the invention in which G is hydrogen, A is methyl and B is isopropyl and X, Y and Z each have the meanings given in Table 1.

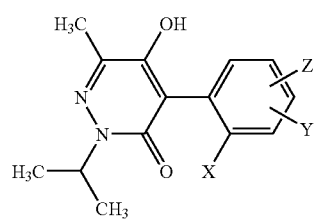

Table 9: Compounds of the general formula (I) according to the invention in which G is hydrogen, A is ethyl and B is methyl and X, Y and Z each have the meanings given in Table 1.

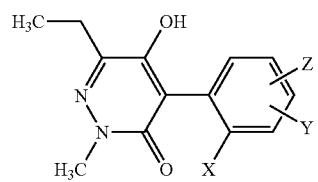

Table 10: Compounds of the general formula (I) according to the invention in which G is hydrogen, A is ethyl and B is ethyl and X, Y and Z each have the meanings given in Table 1.

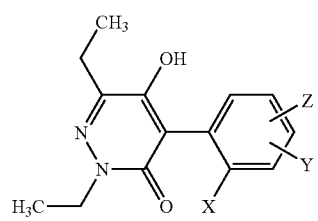

Table 11: Compounds of the general formula (I) according to the invention in which G is hydrogen, A is ethyl and B is n-propyl and X, Y and Z each have the meanings given in Table 1.

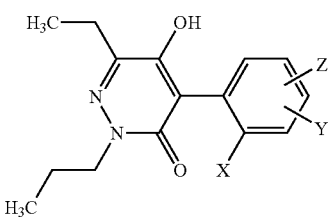

Table 12: Compounds of the general formula (I) according to the invention in which G is hydrogen, A is ethyl and B is isopropyl and X, Y and Z each have the meanings given in Table 1.

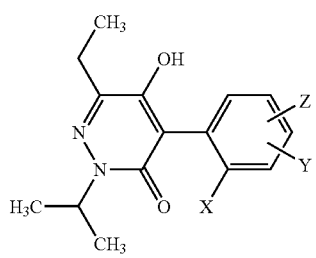

Table 13: Compounds of the general formula (I) according to the invention in which G is hydrogen, and A is propyl and B is methyl and X, Y and Z each have the meanings given in Table 1.

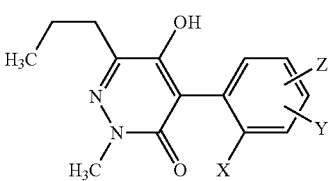

Table 14: Compounds of the general formula (I) according to the invention in which G is hydrogen, A is propyl and B is ethyl and X, Y and Z each have the meanings given in Table 1.

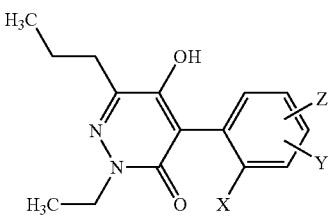

Table 15: Compounds of the general formula (I) according to the invention in which G is hydrogen, A is propyl and B is n-propyl and X, Y and Z each have the meanings given in Table 1.

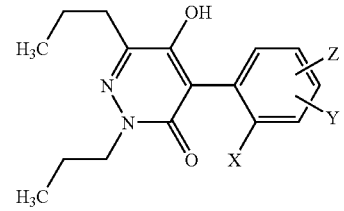

Table 16: Compounds of the general formula (I) according to the invention in which G is hydrogen, A is propyl and B is isopropyl and X, Y and Z each have the meanings given in Table 1.

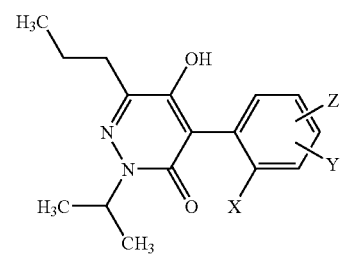

Table 17: Compounds of the general formula (I) according to the invention in which G is hydrogen, and A is isopropyl and B is methyl and X, Y and Z each have the meanings given in Table 1.

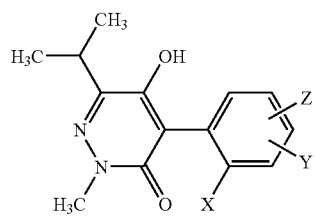

Table 18: Compounds of the general formula (I) according to the invention in which G is hydrogen, A is isopropyl and B is ethyl and X, Y and Z each have the meanings given in Table 1.

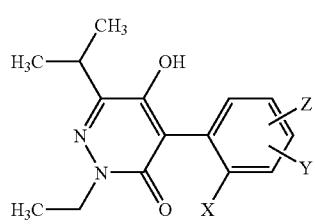

Table 19: Compounds of the general formula (I) according to the invention in which G is hydrogen, A is isopropyl and B is n-propyl and X, Y and Z each have the meanings given in Table 1.

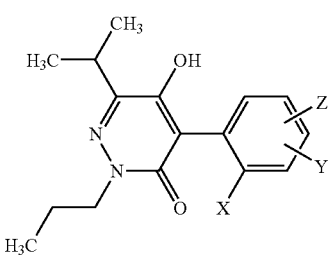

Table 20: Compounds of the general formula (I) according to the invention in which G is hydrogen, A is isopropyl and B is isopropyl and X, Y and Z each have the meanings given in Table 1.

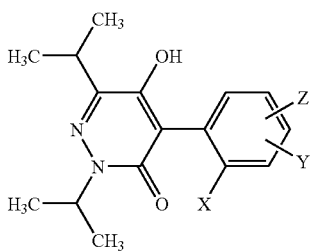

Very particular preference is also given to compounds in Tables 1 to 20 listed above in which G is in each case C(=O)R$^1$, C(=L)LR$^2$, SO$_2$R$^3$, P(=L)R$^4$R$^5$, C(=L)NR$^6$R$^7$ or E.

Collections of compounds of the formula (I) and/or their salts which can be synthesized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning a procedure as described for example by D. Tiebes in Combinatorial Chemistry—Synthesis, Analysis, Screening (Editor Günther Jung), Wiley 1999, on pages 1 to 34.

A number of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Günther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation in accordance with the processes described herein generates compounds of the formula (I) and their salts in the form of substance collections, which are referred to as libraries. The present invention also relates to libraries which comprise at least two compounds of the formula (I) and their salts.

The compounds of the formula (I) according to the invention (and/or their salts), hereinbelow together referred to as "compounds according to the invention", have an outstanding herbicidal activity against a broad spectrum of economically important monocotyledonous and dicotyledonous annual harmful plants. The active substances also act efficiently on perennial harmful plants which produce shoots from rhizomes, rootstocks or other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atri-*

*plex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active substances are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active substances can also be employed for controlling harmful plants in crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

It is preferred to use the compounds according to the invention or their salts in economically important transgenic crops of useful plants and ornamentals, for example of cereals such as wheat, barley, rye, oats, sorghum and millet, rice, cassava and corn or else crops of sugar beet, cotton, soybean, oil seed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active substances according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium polyacrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active compound of the formula (I). In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to prepare combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers. In this context, one and in some cases also several use forms are mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, NC-620, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulf-allate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryne, TH-547, i.e. propyrisulfuron, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and also the following compounds:

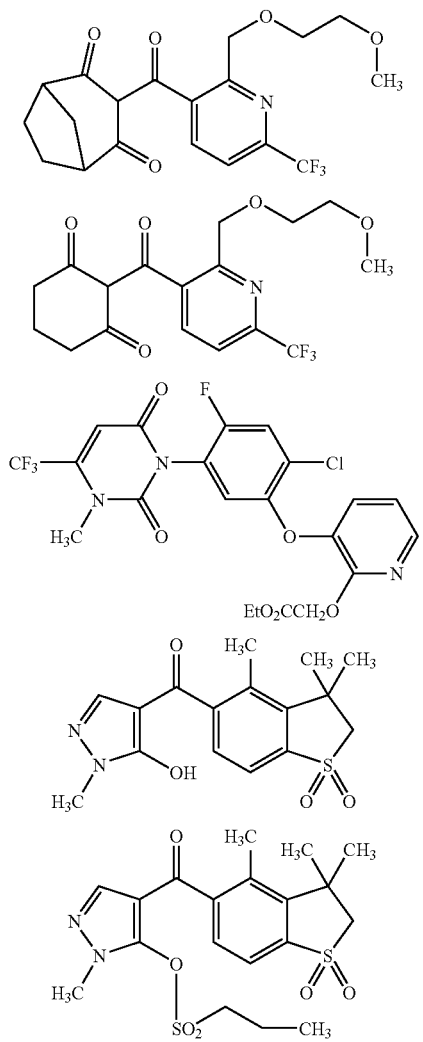

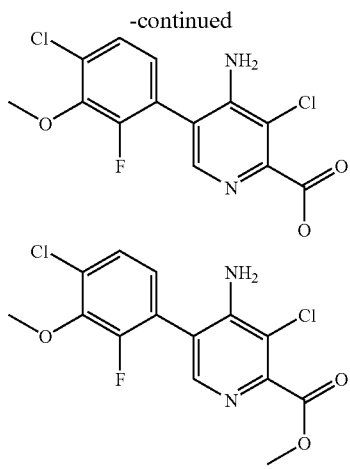

For use, the formulations in commercial form are, if appropriate, diluted in a customary manner, for example in the case of wettable powders, dispersions and water-dispersable granules with water. Preparations in the form of dusts, granules for soil application or granules for broadcasting and sprayable solutions are usually not diluted with other inert substances prior to application.

The application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably is it between 0.005 and 750 g/ha.

In addition to the herbicidal action, the compounds according to the invention also have good insecticidal action. Accordingly, the invention also relates to their use as insecticides.

The examples below serve to illustrate the invention.

Chemical Examples

1. Preparation of 4-(2-chloro-6-fluorophenyl)-5-hydroxy-2,6-dimethyl-3(2H)pyridazinone (No. 1 of Table 21)

A solution of 2.1 g (2 eq) of potassium t-butoxide in 10 ml of DMF was initially charged, and 2.8 g (9.4 mmol) of ethyl 2-{[2-(2-chloro-6-fluorophenyl)acetyl]methylhydrazono}propionate in 10 ml of DMF was slowly added dropwise at <0° C. The mixture was allowed to warm to RT and then stirred for a further 0.5 hour. The reaction solution was then poured into 100 ml of cooled 1N hydrochloric acid and extracted twice with in each case 250 ml of ethyl acetate. The combined organic phases were washed with 50 ml of saturated sodium chloride solution and then dried with sodium sulfate, concentrated under reduced pressure and purified by column chromatography (silica gel, ethyl acetate/n-heptane gradient). This gave 1.2 g of pure product.

2. Preparation of 4-(3,4-dichlorophenyl)-5-hydroxy-2-methyl-3(2H)-pyridazinone (No. 4 of Table 21)

4 ml of water/ethanediol (1:1) were added to 1.0 g (7.4 mmol) of 4-(3,4-dichlorophenyl)-5-methoxy-2-methyl-2H-pyridazin-3-one and 0.4 g of potassium hydroxide (2 eq), and the mixture was reacted at 150° C. overnight. The reaction mixture was added to 50 ml of water and adjusted to pH 1 using concentrated hydrochloric acid, and the resulting precipitate was filtered off. Recrystallization from isopropanol gave 0.2 g of pure product.

The following compounds were prepared analogously to Examples 1 and 2 mentioned above:

TABLE 21

Compounds of the general formula (I) according to the invention in which G is hydrogen.

(I-a)

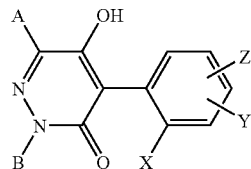

| No. | X | Y | Z | A | B | Analytical data |
|---|---|---|---|---|---|---|
| I-1-a-1 | Cl | 6-F | H | Me | Me | 1H-NMR, 400 MHz, d6-DMSO, 10.88 (bs, 1H), 7.48 (m, 1H), 7.40 (dd, 1H), 7.27 (t, 1H) 3.58 (s, 3H), 2.23 (s, 3H) |
| I-1-a-2 | NO$_2$ | H | H | Me | Me | 1H-NMR, 400 MHz, d6-DMSO, 10.7 (bs, 1H), 8.10 (d, 1H), 7.78 (t, 1H), 7.62 (t, 1H), 7.45 (d, 1H) 3.53 (s, 3H), 2.28 (s, 3H) |
| I-1-a-3 | Cl | 3-Cl | H | Me | Me | 1H-NMR, 400 MHz, d6-DMSO, 10.58 (bs, 1H), 7.58 (d, 1H), 7.42 (t, 1H), 7.25 (d, 1H) 3.58 (s, 3H), 2.21 (s, 3H) |
| I-1-a-4 | H | 4-Cl | 3-Cl | H | Me | mp.: 315° C. |
| I-1-a-5 | Cl | H | 4-Cl | H | t-Bu | mp.: 250° C. |
| I-1-a-6 | Cl | 6-Cl | H | Me | Me | 1H-NMR, 400 MHz, d6-DMSO, 10.8 (bs, 1H), 7.52 (pseudo d, 2H), 7.43 (t, 1H), 3.58 (s, 3H), 2.23 (s, 3H) |
| I-1-a-7 | H | 3-Ph | H | H | t-Bu | mp.: 244° C. |
| I-1-a-8 | H | 5-CF$_3$ | 3-CF$_3$ | H | t-Bu | mp.: 239° C. |
| I-1-a-9 | Cl | 4-Me | 6-Br | Me | Me | 1H-NMR, 400 MHz, d6-DMSO, 10.65 (bs, 1H), 7.52 (s, 1H), 7.38 (s, 1H), 3.57 (s, 3H), 2.33 (s, 3H), 2.23 (s, 3H) |

TABLE 21-continued

Compounds of the general formula (I) according to the invention in which G is hydrogen.

(I-a)

| No. | X | Y | Z | A | B | Analytical data |
|---|---|---|---|---|---|---|
| I-1-a-10 | Cl | 5-(4-Cl-Ph) | H | H | t-Bu | mp.: 250° C. |
| I-1-a-11 | Br | 4-Me | Br | Me | Me | 1H-NMR, 400 MHz, d6-DMSO, 7.56 (s, 2H), 3.58 (s, 3H), 2.32 (s, 3H), 2.23 (s, 3H) |
| I-1-a-12 | Cl | H | 3-Cl | H | t-Bu | amorphous powder |
| I-1-a-13 | Cl | 6-Cl | H | i-Bu | Me | 1H-NMR, 400 MHz, d6-DMSO, 10.8 (bs, 1H), 7.52 (d, 2H), 7.43 (t, 1H), 3.56 (s, 3H), 2.51 (m, 2H, obscured by solvent), 2.03 (m, 1H), 0.90 (d, 6H) |
| I-1-a-14 | Cl | 4-OCF$_3$ | 6-Cl | Me | Me | 1H-NMR, 400 MHz, d6-DMSO, 11.0 (bs, 1H), 7.72 (s, 2H), 3.58 (s, 3H), 2.23 (s, 3H) |
| I-1-a-15 | Cl | 4-Me | 6-c-Pr | Me | Me | 1H-NMR, 400 MHz, d6-DMSO, 7.07 (s, 1H), 6.82 (s, 1H), 3.53 (s, 3H), 2.40 (s, 3H), 2.28 (s, 3H), 1.81 (m, 1H), 0.89 (m, 2H), 0.63 (m, 2H) |
| I-1-a-16 | Cl | 4-Me | 6-OCF$_3$ | Me | Me | 1H-NMR, 400 MHz, d6-DMSO, 7.42 (s, 1H), 7.23 (s, 1H), 3.56 (s, 3H), 2.41 (s, 3H), 2.22 (s, 3H) |
| I-1-a-17 | F | 3-Me | 6-F | Me | Me | 1H-NMR, 400 MHz, d6-DMSO, 7.37 (q, 1H), 7.03 (t, 1H), 3.56 (s, 3H), 2.23 (pseudo d, 6H) |
| I-1-a-18 | Cl | 3-Me | 6-F | Me | Me | 1H-NMR, 400 MHz, d6-DMSO, 7.37 (t, 1H), 7.12 (t, 1H), 3.52 (s, 3H), 2.32 (s, 3H), 2.23 (s, 3H) |
| I-1-a-19 | F | 3-OMe | 6-F | Me | Me | 1H-NMR, 400 MHz, d6-DMSO, 7.17 (m, 1H), 7.02 (t, 1H), 3.82 (s, 3H), 3.54 (s, 3H), 2.18 (s, 3H) |
| I-1-a-20 | Cl | 4-Br | 6-Cl | Me | Me | 1H-NMR, 400 MHz, d6-DMSO, 7.82 (s, 2H), 3.54 (s, 3H), 2.21 (s, 3H) |
| I-1-a-21 | F | 6-F | H | Me | H | 1H-NMR, 400 MHz, d6-DMSO, 7.50 (m, 1H), 7.12 (m, 1H), 2.23 (pseudo d, 6H) |
| I-1-a-22 | Cl | 6-CF$_3$ | H | Me | Me | 1H-NMR, 400 MHz, d6-DMSO, 10.75 (bs, 1H), 7.88 (d, 1H), 7.81 (d, 1H), 7.67 (t, 1H), 3.56 (s, 3H), 2.23 (s, 3H) |
| I-1-a-23 | Cl | 4-Cl | 6-Br | Me | Me | 1H-NMR, 400 MHz, d6-DMSO, 10.75 (bs, 1H), 7.88 (s, 1H), 7.68 (t, 1H), 3.58 (s, 3H), 2.23 (s, 3H) |
| I-1-a-24 | F | 3-F | H | Me | Me | 1H-NMR, 400 MHz, d6-DMSO, 10.8 (bs, 1H), 7.43 (m, 1H), 7.23 (m, 1H), 7.11 (m, 1H), 3.58 (s, 3H), 2.22 (s, 3H) |
| I-1-a-25 | OCF$_3$ | 4-Br | 6-Br | Me | Me | 1H-NMR, 400 MHz, d6-DMSO, 7.92 (s, 1H), 7.59 (s, 1H), 3.48 (s, 3H), 2.11 (s, 3H) |
| I-1-a-26 | I | H | H | Me | Me | 1H-NMR, 400 MHz, d6-DMSO, 7.92 (d, 1H), 7.42 (t, 1H), 7.15 (m, 2H), 3.56 (s, 3H), 2.24 (s, 3H) |
| I-1-a-27 | Cl | 4-Cl | H | Me | Me | 1H-NMR, 400 MHz, d6-DMSO, 10.54 (bs, 1H), 7.72 (d, 1H), 7.48 (dd, 1H), 7.16 (d, 1H) 3.58 (s, 3H), 2.23 (s, 3H) |
| I-1-a-28 | H | 4-Cl | H | Me | Me | 1H-NMR, 400 MHz, d6-DMSO, 10.4 (bs, 1H), 7.50 (pseudo s, 4 H), 3.59 (s, 3H), 2.24 (s, 3H) |
| I-1-a-29 | H | 3-Cl | H | Me | Me | 1H-NMR, 600 MHz, d6-DMSO, 10.4 (bs, 1H), 7.47 (m, 3H) 7.39 (d, 2H), 3.61 (s, 3H), 2.27 (s, 3H) |
| I-1-a-30 | H | 3-CF$_3$ | H | Me | Me | 1H-NMR, 400 MHz, CDCl$_3$, 10.54 (bs, 1H), 7.72 (d, 1H), 7.75-7.55 (m, 4H), 3.71 (s, 3H), 2.31 (s, 3H) |
| I-1-a-31 | Cl | H | H | Me | Me | 1H-NMR, 600 MHz, d6-DMSO, 10.4 (bs, 1H), 7.49 (m, 2H) 7.44 (d, 2 H), 7.41 (d, 2 H), 3.59 (s, 3H), 2.24 (s, 3H) |

TABLE 21-continued

Compounds of the general formula (I) according to the invention in which G is hydrogen.

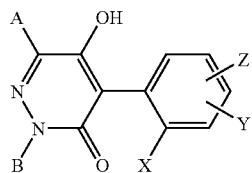

(I-a)

| No. | X | Y | Z | A | B | Analytical data |
|---|---|---|---|---|---|---|
| I-1-a-32 | Cl | 6-F | H | Me | H | 1H-NMR 400 MHz, d6-DMSO: 12.27 ppm (broad s, 1H), 7.41-7.47 (m, 1H); 7.36 (d, 1H); 7.19-7.23 (m, 1H); 2.22 (s, 3H) |
| I-1-a-33 | Cl | 6-F | 4-F | Me | H | oil |
| I-1-a-34 | Cl | 6-Cl | 4-Cl | Me | H | 1H-NMR 400 MHz, d6-DMSO: 12.27 ppm ((broad s, 1H), 7.66 (s, 2H); 2.20 (s, 3H) |
| I-1-a-35 | Cl | 6-F | 3-Me | Me | H | 1H-NMR 400 MHz, d6-DMSO: 12.27 ppm (broad s, 1H), 7.23-7.33 (m, 2H); 2.49 (s, 3H); 2.48 (s, 3H) |
| I-1-a-36 | F | 6-F | 3-F | Me | H | 1H-NMR 400 MHz, d6-DMSO: 12.38 ppm (broad s, 1H), 7.50 (ddd, 1H); 7.10-7.16 (m, 1H); 2.22 (s, 3H), |

3. Preparation of 5-isopropoxy-4-(2-chloro-6-fluorophenyl)-2,6-dimethyl-3(2H)-pyridazinone (No. 1 of Table 22)

0.15 g (0.55 mmol) of the compound I-1-a-1 according to the invention of Table 21 and 0.07 g of triethylamine (1.3 eq) were initially charged in 10 ml of dichloromethane. 0.06 g (1.0 eq) of isobutyryl chloride was then added dropwise over a period of 10 min. The mixture was stirred for one hour, and 10 ml of 5 percent sodium bicarbonate solution were added. The organic phase was separated off and then dried giving, after chromatographic purification (silica gel, gradient ethyl acetate/n-heptane), 0.18 g.

The compounds of Table 22 can be obtained analogously to the method mentioned above.

TABLE 22

Compounds of the general formula (I) according to the invention in which G is C(=O)R$^1$.

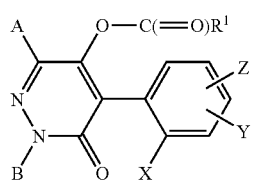

(I-b)

| No. | X | Y | Z | R$^1$ | A | B | Analytical data |
|---|---|---|---|---|---|---|---|
| I-1-b-1 | Cl | 6-F | H | i-Pr | Me | Me | 1H-NMR, 400 MHz, d6-DMSO, 7.53 (m, 1H), 7.47 (d, 1H), 7.35 (t, 1H) 3.71 (s, 3H), 2.65 (m, 1H), 2.20 (s, 3H), 0.88 (m, 6H) |
| I-1-b-2 | H | 3-Cl | 4-Cl | i-Pr | Me | H | 89° C. |
| I-1-b-3 | Cl | 6-Cl | H | i-Pr | Me | Me | 1H-NMR, 400 MHz, d6-DMSO, 7.60 (pseudo d, 2H), 7.50 (t, 1H), 3.72 (s, 3H), 2.62 (m, 1H), 2.20 (s, 3H), 0.86 (d, 6H) |
| I-1-b-4 | NO$_2$ | H | H | i-Pr | Me | Me | 1H-NMR, 400 MHz, d6-DMSO, 8.20 (d, 1H), 7.88 (t, 1H), 7.72 (t, 1H), 7.38 (d, 1H) 3.67 (s, 3H), 2.65 (m, 1H), 2.19 (s, 3H), 0.92 (m, 6H) |
| I-1-b-5 | F | 3-F | H | i-Pr | Me | Me | 1H-NMR, 400 MHz, d6-DMSO, 7.55 (m, 1H), 7.30 (m, 1H), 7.07 (m, 1H), 3.70 (s, 3H), 2.68 (m, 1H), 2.19 (s, 3H), 0.93 (m, 6H) |

TABLE 22-continued

Compounds of the general formula (I)
according to the invention in
which G is C(=O)R$^1$.

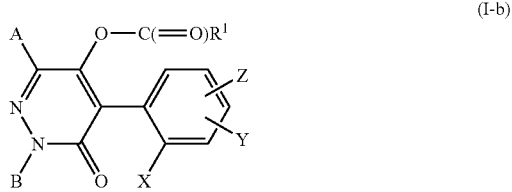

(I-b)

| No. | X | Y | Z | R$^1$ | A | B | Analytical data |
|---|---|---|---|---|---|---|---|
| I-1-b-6 | Cl | 4-Me | 6-Br | i-Pr | Me | Me | 1H-NMR, 400 MHz, d6-DMSO, 7.58 (s, 1H), 7.44 (s, 1H), 3.71 (s, 3H), 2.31 (s, 3H), 2.19 (s, 3H) |
| I-1-b-7 | Cl | 4-OCF$_3$ | 6-Cl | i-Pr | Me | Me | 1H-NMR, 400 MHz, CDCl$_3$, 7.32 (s, 2H), 3.85 (s, 3H), 2.62 (m, 1H), 2.28 (s, 3H), 1.01 (d, 6H) |
| I-1-b-8 | Br | 4-Me | 6-Br | i-Pr | Me | Me | 1H-NMR, 400 MHz, CDCl$_3$, 7.41 (s, 2H), 3.82 (s, 3H), 2.58 (m, 1H), 2.32 (s, 3H), 2.25 (s, 3H), 0.99 (d, 6H) |
| I-1-b-9 | Cl | 3-Cl | H | i-Pr | Me | Me | 1H-NMR, 400 MHz, CDCl$_3$, 7.50 (d, 1H), 7.25 (t, 1H), 7.09 (d, 1H) 3.82 (s, 3H), 2.57 (m, 1H), 2.25 (s, 3H), 1.00 (dd, 6H) |
| I-1-b-10 | Cl | 4-Me | 6-OCF$_3$ | i-Pr | Me | Me | 1H-NMR, 400 MHz, CDCl$_3$, 7.21 (s, 1H), 7.02 (s, 1H), 3.75 (s, 3H), 2.57 (m, 1H), 2.38 (s, 6H), 0.99 (m, 6H) |
| I-1-b-11 | F | 3-Me | 6-F | Et | Me | Me | 1H-NMR, 400 MHz, d6-DMSO, 7.43 (m, 1H), 7.12 (t, 1H), 3.68 (s, 3H), 2.40 (t, 1H), 2.21 (s, 6H), 0.89 (m, 6H) |
| I-1-b-12 | Cl | 3-Me | 6-F | Me | Me | Me | 1H-NMR, 400 MHz, d6-DMSO, 7.52 (m, 1H), 7.22 (t, 1H), 3.70 (s, 3H), 2.32 (s, 3H), 2.22 (s, 3H), 2.09 (s, 3H) |
| I-1-b-13 | Cl | 4-Br | 6-Cl | i-Pr | Me | Me | 1H-NMR, 400 MHz, d6-DMSO, 7.96 (s, 2H), 3.72 (s, 3H), 2.70 (m, 1H), 2.23 (s, 3H), 0.92 (m, 6H) |
| I-1-b-14 | Cl | 4-Cl | 6-Br | Me | Me | Me | 1H-NMR, 400 MHz, d6-DMSO, 7.96 (d, 1H), 7.88 (d, 1H), 3.71 (s, 3H), 2.23 (s, 3H), 2.12 (s, 3H) |
| I-1-b-15 | Cl | 4-Me | 6-c-Pr | Me | Me | Me | 1H-NMR, 400 MHz, d6-DMSO, 7.58 (d, 1H), 7.22 (d, 1H), 3.68 (s, 3H), 2.29 8s, 3H), 2.21 (s, 3H), 2.05 (s, 3H) |
| I-1-b-16 | Cl | 6-Cl | H | i-Pr | i-Bu | Me | 1H-NMR, 400 MHz, CDCl$_3$, 7.39 (d, 2H), 7.28 (t, 1H), 3.87 (s, 3H), 2.53 (m, 1H), 2.42 (d, 2H), 2.06 (m, 1H), 0.96 (m, 12H) |

4. Preparation of 4-(2,6-dichlorophenyl)-5-ethoxy-carbonyloxy-2-methyl-6-isobutyl-3(2H)-pyridazi-none (No. 1 of Table 23)

0.5 g (1.52 mmol) of the compound I-1-a-13 according to the invention of Table 21 was initially charged in 25 ml of dichloromethane, and 0.2 g of triethylamine and 0.18 g of ethyl chloroformate were added. The mixture was stirred at RT for 15 min and then added to 30 ml of five percent strength sodium bicarbonate solution. The organic phase was separated off and then dried, concentrated and purified by column chromatography (silica gel, gradient ethyl acetate/n-heptane). This gave 0.47 g.

The compounds of Table 23 can be obtained analogously to the methods mentioned above.

TABLE 23

Compounds of the general formula (I) according to the invention in which G is C(=L)MR².

$$\text{(I-c)}$$

| No. | X | Y | Z | A | B | L | M | R² | Analytical data |
|---|---|---|---|---|---|---|---|---|---|
| I-1-c-1 | Cl | 6-Cl | H | i-Bu | Me | O | O | Et | 1H-NMR, 400 MHz, CDCl₃, 7.40 (d, 2H), 7.29 (t, 1H), 4.13 (q, 2H), 3.84 (s, 3H), 2.51 (d, 2H), 2,10 (m, 1H), 1.15 (t, 3H), 0.96 (d, 6H) |
| I-1-c-2 | F | 3-Me | 6-F | Me | Me | O | O | Et | 1H-NMR, 400 MHz, CDCl₃, 7.46 (q 1H), 7.13 (t, 1H), 4.32 (q, 2H), 3.82 (s, 3H), 2.22 (s, 3H), 1.32 (t, 3H) |
| I-1-c-3 | F | 3-OMe | 6-F | Me | Me | O | O | Et | 1H-NMR, 400 MHz, d6-DMSO, 7.32 (m, 1H), 7.17 (t, 1H), 4.13 (q, 2H), 3.85 (s, 3H), 3.71 (s, 3H), 2.25 (s, 3H), 1.09 (t, 3H) |
| I-1-c-4 | Cl | 6-Br | 4-Me | Me | Me | O | O | Et | 1H-NMR, 400 MHz, d6-DMSO, 7.59 (s, 1H), 7.47 (s, 1H), 4.16 (q, 2H), 3.71 (s, 3H), 2.35 (s, 3H), 2.25 (s, 3H), 1.12 (t, 3H) |
| I-1-c-5 | NO₂ | H | H | Me | Me | O | O | Et | 1H-NMR, 400 MHz, d6-DMSO, 8.23 (d, 1H), 7.88 (t, 1H), 7.75 (t, 1H), 7.43 (d, 1H), 4.15 (m, 2H), 3.68 (s, 3H), 2.28 (s, 3H), 0.92 (m, 6H) |
| I-1-c-6 | Cl | 3-Cl | H | Me | Me | O | O | Et | 1H-NMR, 400 MHz, DMSO, 7.72 (d, 1H), 7.47 (t, 1H), 7.22 (d, 1H), 4.13. (q, 2H), 3.72 (s, 3H), 2.25 (s, 3H), 1.07 (t, 3H) |
| I-1-c-7 | Cl | 6-F | H | Me | Me | O | O | Et | 1H-NMR, 400 MHz, d6-DMSO, 7.58 (m, 1H), 7.49 (d, 1H), 7.38 (t, 1H) 3.71 (s, 3H), 2.28 (s, 3H), 1.08 (t, 3H) |
| I-1-c-8 | Cl | 6-Cl | H | Me | Me | O | O | Et | 1H-NMR, 400 MHz, CDCl₃, 7.60 (d, 2H), 7.52 (t, 1H), 4.13 (q, 2H), 3.72 (s, 3H), 2.28 (s, 3H), 1.15 (t, 3H) |
| I-1-c-9 | Cl | 4-Cl | H | Me | Me | O | O | Et | 1H-NMR, 400 MHz, d6-DMSO, 7.79 (d, 1H), 7.53 (dd, 1H), 7.28 (d, 1H), 4.16 (q, 2H), 3.70 (s, 3H), 2.23 (s, 3H), 1.12 (t, 3H) |
| I-1-c-10 | F | 3-F | H | Me | Me | O | O | Et | 1H-NMR, 400 MHz, d6-DMSO, 7.57 (m, 1H), 7.32 (m, 1H), 7.13 (m, 1H), 4.13 (q, 2H), 3.71 (s, 3H), 2.25 (s, 3H), 1.08 (t, 3H) |
| I-1-c-11 | Br | 6-Br | 4-Me | Me | Me | O | O | Et | 1H-NMR, 400 MHz, d6-DMSO, 7.61 (s, 2H), 4.18 (q, 2H), 3.72 (s, 3H), 2.33 (s, 3H), 2.26 (s, 3H), 1.11 (t, 3H) |
| I-1-c-12 | Cl | 6-Cl | 4-OCF₃ | Me | Me | O | O | Et | 1H-NMR, 400 MHz, CDCl3, 7.82 (s, 2H), |

TABLE 23-continued

Compounds of the general formula (I) according to the invention in which G is C(=L)MR².

(I-c)

| No. | X | Y | Z | A | B | L | M | R² | Analytical data |
|---|---|---|---|---|---|---|---|---|---|
| I-1-c-13 | Cl | 6-OCF₃ | 4-Me | Me | Me | O | O | Et | 4.17 (q, 2H,) 3.72 (s, 3H) 2.28 (s, 3H), 1.07 (t, 3H) 1H-NMR, 400 MHz, d6-DMSO, 7.48 (s, 1H), 7.32 (s, 1H), 4.18 (q, 2H), 3.71 (s, 3H), 2.42 (s, 3H), 2.21 (s, 3H), 1.12 (t, 3H) |
| I-1-c-14 | OCF₃ | 4-Br | 6-Br | Me | Me | O | O | Et | 1H-NMR, 400 MHz, d6-DMSO, 8.18 (s, 1H), 7.82 (s, 1H), 4.18 (q, 2H), 3.72 (s, 3H), 2.26 (s, 3H), 1.13 (t, 3H) |
| I-1-c-15 | H | 3-CF₃ | H | Me | Me | O | O | Et | 1H-NMR, 400 MHz, CDCl₃, 7.72 (d, 1H), 7.70-7.55 (m, 4H), 4.13 (q, 2H), 3.81 (s, 3H), 2.31 (s, 3H), 1.17 (t, 3H) |
| I-1-c-16 | Cl | 3-Me | 6-F | Me | Me | O | O | Et | 1H-NMR, 400 MHz, d6-DMSO, 7.52 (t, 1H), 7.28 (t, 1H), 4.12 (q, 2H), 3.72 (s, 3H), 2.35 (s, 3H), 2.28 (s, 3H), 1.08 (t, 3H) |
| I-1-c-17 | Cl | 4-Br | 6-Cl | Me | Me | O | O | Et | 1H-NMR, 400 MHz, d6-DMSO, 7.95 (s, 2H), 4.18 (q, 2H), 3.71 (s, 3H), 2.27 (s, 3H), 1.13 (t, 3H) |
| I-1-c-18 | CF3 | 6-Cl | H | Me | Me | O | O | Et | 1H-NMR, 400 MHz, d6-DMSO, 7.97 (d, 1H), 7.89 (d, 1H), 7.73 (t, 1H), 4.16 (q, 2H), 3.73 (s, 3H), 2.28 (s, 3H), 1.12 (t, 3H) |
| I-1-c-19 | I | H | H | Me | Me | O | O | Et | 1H-NMR, 400 MHz, d6-DMSO, 7.95 (d, 1H), 7.48 (t, 1H), 7.20 (t, 1H), 7.12 (d, 1H), 4.13 (q, 2H), 3.71 (s, 3H), 2.24 (s, 3H), 1.10 (t, 3H) |
| I-1-c-20 | Cl | 4-Me | 6-Br | Me | Me | O | O | Me | 1H-NMR, 400 MHz, d6-DMSO, 7.60 (d, 1H), 7.46 (d, 1H), 3.75 (s, 3H), 3.72 (s, 3H), 2.37 (s, 3H), 2.26 (s, 3H) |
| I-1-c-21 | Cl | 3-Me | 6-F | Me | Me | O | O | Me | 1H-NMR, 400 MHz, d6-DMSO, 7.52 (t, 1H), 7.28 (t, 1H), 3.72 (s, 6H), 2.35 (s, 3H), 2.28 (s, 3H) |
| I-1-c-22 | F | 3-F | H | Me | Me | O | O | Bzl | 1H-NMR, 400 MHz, d6-DMSO, 7.53 (m, 1H), 7.38 (m, 3H), 7.25 (m, 1H), 7.19 (m, 2H), 7.13 (m, 1H), 5.18 (s, 2H), 3.71 (s, 3H), 2.23 (s, 3H) |
| I-1-c-23 | Cl | 3-Cl | H | Me | Me | O | O | iBu | 1H-NMR, 400 MHz, DMSO, 7.72 (d, 1H), 7.46 (t, 1H), 7.22 (d, 1H), 3.93. (m, 2H), 3.71 (s, 3H), 2.25 (s, 3H), 1.72 (m, 1H), 0.72 (d, 6H) |

TABLE 23-continued

Compounds of the general formula (I) according to the invention in which G is C(=L)MR².

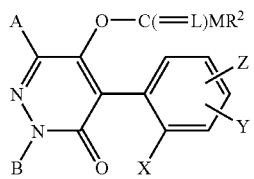

(I-c)

| No. | X | Y | Z | A | B | L | M | R² | Analytical data |
|---|---|---|---|---|---|---|---|---|---|
| I-1-c-24 | Cl | 4-Me | 6-OCF₃ | Me | Me | O | O | All | 1H-NMR, 400 MHz, d6-DMSO, 7.49 (s, 1H), 7.32 (s, 1H), 5.78 (m, 1H), 5.18 (m, 2H), 4.62 (d, 2H), 3.71 (s, 3H), 2.40 (s, 3H), 2.26 (s, 3H) |
| I-1-c-25 | Cl | 6-Cl | H | i-Bu | Me | O | O | All | 1H-NMR, 400 MHz, CDCl₃, 7.39 (d, 2H), 7.32 (t, 1H), 5.72 (m, 1H), 5.20 (m, 2H), 4.53 (d, 2H), 3.84 (s, 3H), 2.50 (d, 2H), 2.09 (m, 1H), 0.97 (d, 6H) |

5. Preparation of 4-(2-chlorophenyl)-5-methylsulfonyloxy-2,6-dimethyl-3(2H)-pyridazinone (No. 1 of Table 24)

0.03 g (0.12 mmol) of the compound I-1-a-31 according to the invention of Table 21 was initially charged in 10 ml of ethyl acetate, 0.02 g of triethylamine and a spatula tip of DMAP were added and the mixture was warmed to 60° C. 0.015 g of methanesulfonyl chloride in 2 ml of ethyl acetate was then added, and the mixture was stirred for 1 hour. After addition of 6 ml of saturated sodium chloride solution, the organic phase was dried, concentrated and purified by column chromatography (silica gel, gradient ethyl acetate/n-heptane). This gave 0.02 g of pure product.

The compounds of Table 24 can be obtained analogously to the methods mentioned above.

TABLE 24

Compounds of the general formula (I) according to the invention in which G is SO₂R³.

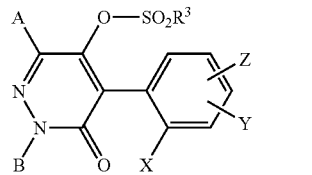

(I-d)

| No. | X | Y | Z | R³ | A | B | Analytical data |
|---|---|---|---|---|---|---|---|
| I-1-d-1 | Cl | H | H | Me | Me | Me | 1H-NMR, 400 MHz, CDCl₃, 7.55 (s, 1H), 7.42 (pseudo t, 3H), 3.81 (s, 3H), 2.51 (s, 3H), 2.48 (s, 3H) |
| I-1-d-2 | Cl | 6-F | H | Me | Me | Me | 1H-NMR, 400 MHz, d6-DMSO, 7.58 (m, 1H), 7.49 (d, 1H), 7.37 (t, 1H) 3.73 (s, 3H), 3.15 (s, 3H), 2.39 (t, 3H) |
| I-1-d-3 | Cl | 4-Me | 6-Br | Me | Me | Me | 1H-NMR, 400 MHz, d6-DMSO, 7.61 (s, 1H), 7.48 (s, 1H), 3.71 (s, 3H), 3.11 (s, 3H), 2.38 (s, 3H), 2.33 (s, 3H) |
| I-1-d-4 | NO₂ | H | H | Me | Me | Me | 1H-NMR, 400 MHz, d6-DMSO, 8.23 (d, 1H), 7.88 (t, 1H), 7.77 (t, 1H), 7.60 (d, 1H) 3.67 (s, 3H), 3.05 (s, 3H), 2.39 (s, 3H) |
| I-1-d-5 | Cl | 4-Br | 6-Cl | Me | Me | Me | 1H-NMR, 400 MHz, d6-DMSO, 7.96 (s, 2H), 3.71 (s, 3H), 3.35 (s, 3H), 2.40 (s, 3H) |

TABLE 24-continued

Compounds of the general formula (I) according to the invention in which G is SO₂R³.

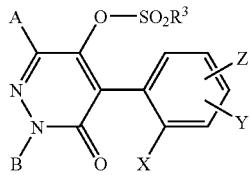

(I-d)

| No. | X | Y | Z | R³ | A | B | Analytical data |
|---|---|---|---|---|---|---|---|
| I-1-d-6 | F | 3-F | H | Tolyl | Me | Me | 1H-NMR, 400 MHz, d6-DMSO: 7.43 (d, 2H); 7.33 (m, 1H), 7.25 (d, 2H), 7.09 (m, 1H), 7.02 (m, 1H), 3.68 (s, 3H), 2.38 (s, 3H), 2.35 (s, 3H) |
| I-1-d-7 | Cl | 4-OCF₃ | 6-Cl | Et | Me | Me | 1H-NMR, 400 MHz, d6-DMSO, 7.82 (s, 2H), 3.72 (s, 3H), 3.33 (q, 2H), 2.40 (s, 3H), 1.08 (t, 3H) |
| I-1-d-8 | F | 3-OCH₃ | 6-F | Me | Me | Me | 1H-NMR, 400 MHz, d6-DMSO: 7.33 (m, 1H); 7.18 (m, 1H), 3.86 (s, 3H), 3.72 (s, 3H), 3.21 (s, 3H), 2.41 (s, 3H) |
| I-1-d-9 | Cl | 6-Cl | H | Me | i-Bu | Me | 1H-NMR, 400 MHz, CDCl₃, 7.45 (d, 2H), 7.32 (t, 3H), 3.85 (s, 3H), 2.71 (d, 2H), 2.61 (s, 3H), 0.99 (d, 6H) |

6. Preparation of the sodium salt of 4-(2-bromo-6-chloro-4-methylphenyl)-5-hydroxy-2,6-dimethyl-3(2H)-pyridazinone (No. 1 of Table 25)

0.1 g (0.12 mmol) of the compound I-1-a-9 according to the invention of Table 21 and 0.011 g of sodium hydroxide were dissolved in 10 ml of anhydrous methanol and stirred for 1 hour. The mixture was concentrated under reduced pressure and taken up in toluene. The solvent was removed once more, giving an amorphous powder.

The compounds of Table 25 can be obtained analogously to the methods mentioned above.

TABLE 25

Compounds of the general formula (I) according to the invention in which G is E

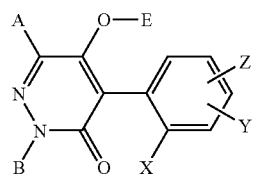

(I-g)

| No. | X | Y | Z | E | A | B | Analytical data |
|---|---|---|---|---|---|---|---|
| I-1-g-1 | Br | 4-Me | 6-Cl | Na⁺ | Me | Me | 1H-NMR, 400 MHz, d6-DMSO, 7.32 (s, 1H), 7.18 (s, 1H), 3.38 (s, 3H), 2.28 (s, 3H), 1.92 (s, 3H) |
| I-1-g-2 | NO₂ | H | H | Na⁺ | Me | Me | 1H-NMR, 400 MHz, d6-DMSO, 7.78 (d, 1H), 7.65 (t, 1H), 7.43 (t, 1H), 7.20 (d, 1H) 3.18 (s, 3H), 1.93 (s, 3H) |
| I-1-g-3 | NO₂ | H | H | (Me)₄N⁺ | Me | Me | 1H-NMR, 400 MHz, d6-DMSO, 7.78 (d, 1H), 7.65 (t, 1H), 7.43 (t, 1H), 7.22 (d, 1H) 3.38 (s, 3H), 3.12 (s, 12H), 1.95 (s, 3H) |
| I-1-g-4 | F | 3-F | H | (Me)₄N⁺ | Me | Me | 1H-NMR, 400 MHz, d6-DMSO, 7.08 (m, 1H), 6.98 (m 1H), 7.13 (m, 1H), 3.38 (s, 3H), 3.13 (s, 12H), 1.96 (s, 3H) |

7. Exemplary description of the preparation of compounds of the formula (II)

Example 1

0.45 g (9.7 mmol) of methylhydrazine, together with 0.99 g of triethylamine and 0.06 g of DMAP (0.05 eq), was initially charged in 50 ml of dichloromethane. 2.2 g of 2,6-dichlorophenylacetyl chloride, freshly prepared from 2,6-dichlorophenylacetic acid and oxalyl chloride, in 50 ml of dichloromethane were slowly added dropwise at 0° C. The mixture was then stirred at room temperature overnight, and ammonium chloride solution was added. The organic phase was separated off, dried and concentrated. Purification by column chromatography gave 1.5 g of 1-(2,6-dichlorophenylacetic acid) 1-methylhydrazide.

1.43 g of methyl pyruvate were added, and the mixture was dissolved in 20 ml of ethanol. The reaction mixture was heated at the boil under reflux for 2 h and then concentrated under reduced pressure and purified by column chromatography (silica gel, mobile phase n-heptane/ethyl acetate gradient). This gave 1.3 g of methyl 2-{[2-(2,6-dichlorophenyl)acetyl]methylhydrazono}propionate.

Example 2

2 g (10.1 mmol) of 2,4-dichlorphenylacetic acid were initially charged in 50 ml of dichloromethane, 1.1 ml (1.67 eq) of oxalyl chloride and a drop of DMF were added and the mixture was heated at the boil under reflux until the evolution of gas had ceased. The mixture was concentrated under reduced pressure, and two more times, dichloromethane was added and the mixture was concentrated again, and the residue was then taken up in 5 ml of dichloromethane. The solution obtained in this manner was, at 0° C., added dropwise over a period of 20 min to a solution of 1.4 g (1.1 eq) of methyl 2-(methylhydrazono)propionate and 2.9 ml of triethylamine (2.1 eq) in 20 ml of dichloromethane. The mixture was then stirred at room temperature overnight, and 30 ml of water were added. The aqueous phase was removed and the organic phase was concentrated. The residue obtained was purified by column chromatography (silica gel, gradient n-heptane/ethyl acetate). This gave a total of 0.7 g of methyl 2-{[2-(2,4-dichlorophenyl)acetyl]methyl-hydrazono}propionate.

TABLE 26

Compounds of the general formula (II)

| No. | X | Y | Z | A | B | $R^9$ | Analytical data |
|---|---|---|---|---|---|---|---|
| II-a-1 | Cl | 3-Cl | H | Me | Me | Me | $^1$H-NMR (400 MHz, d6-DMSO, shift in ppm): 7.54 (d, 1H), 7.34 (m, 2H), 4.10 (s, 2H), 3.78 (s, 3H), 3.36 (s, 3H), 2.27 (s, 3H) |
| II-a-2 | Cl | 6-F | H | Me | Me | Me | $^1$H-NMR (400 MHz, d6-DMSO, shift in ppm): 7.37 (m, 2H), 7.21 (t, 1H), 4.06 (s, 2H), 3.78 (s, 3H), 3.38 (s, 3H), 2.28 (s, 3H) |
| II-a-3 | Cl | 6-Cl | H | Me | Me | Me | $^1$H-NMR (400 MHz, d6-DMSO, shift in ppm): 7.77 (d, 2H), 7.32 (t, 1H), 4.20 (s, 2H), 3.80 (s, 3H), 3.37 (s, 3H), 2.29 (s, 3H) |
| II-a-4 | Cl | 4-Cl | H | Me | Me | Me | $^1$H-NMR (400 MHz, CDCl$_3$, shift in ppm): 7.45-7.04 (m, 3H), 4.10 (s, 2H), 3.89 (s, 3H), 3.42 (s, 3H), 2.29 (s, 3H) |
| II-a-5 | H | 4-Cl | H | Me | Me | Me | $^1$H-NMR (400 MHz, CDCl$_3$, shift in ppm): 7.45-7.15 (m, 4H), 3.97 (s, 2H), 3.90 (s, 3H), 3.37 (s, 3H), 2.23 (s, 3H) |
| II-a-6 | Cl | H | H | Me | Me | Me | $^1$H-NMR (400 MHz, CDCl$_3$, shift in ppm): 7.45-7.05 (m, 4H), 4.14 (s, 2H), 3.88 (s, 3H), 3.41 (s, 3H), 2.27 (s, 3H) |
| II-a-7 | H | 3-Cl | H | Me | Me | Me | $^1$H-NMR (400 MHz, CDCl$_3$, shift in ppm): 7.40-7.05 (m, 4H), 3.98 (s, 2H), 3.93 (s, 3H), 3.38 (s, 3H), 2.21 (s, 3H) |
| II-a-8 | H | 3-CF$_3$ | H | Me | Me | Me | $^1$H-NMR (400 MHz, CDCl$_3$, shift in ppm): 7.70-7.35 (m, 4H), 4.06 (s, 2H), 3.90 (s, 3H), 3.38 (s, 3H), 2.23 (s, 3H) |
| II-a-9 | Br | 4-Me | 6-Br | Me | Me | Me | $^1$H-NMR (400 MHz, d6-DMSO, shift in ppm): 7.52 (s, 2H), 4.22 (s, 2H), 3.78 (s, 3H), 3.43 (s, 3H), 2.28 (s, 6H) |

TABLE 26-continued

Compounds of the general formula (II)

$$\text{(II)}$$

| No. | X | Y | Z | A | B | $R^9$ | Analytical data |
|---|---|---|---|---|---|---|---|
| II-a-10 | Cl | 4-OCF$_3$ | Cl | Me | Me | Me | $^1$H-NMR (400 MHz, d6-DMSO, shift in ppm): 7.64 (s, 2H), 4.22 (s, 2H), 3.78 (s, 3H), 3.38 (s, 3H), 2.28 (s, 3H) |
| II-a-11 | Cl | 4-Me | 6-c-Pr | Me | Me | Me | $^1$H-NMR (400 MHz, d6-DMSO, shift in ppm): 7.11 (s, 1H), 6.82 (s, 1H), 4.22 (s, 2H), 3.78 (s, 3H), 3.36 (s, 3H), 2.28 (s, 3H), 2.25 (s, 3H), 1.788m, 1H), 0.82 (m, 2H), 0.57 (m, 2H) |
| II-a-12 | Cl | 4-Me | 6-OCF$_3$ | Me | Me | Me | $^1$H-NMR (400 MHz, d6-DMSO, shift in ppm): 7.38 (s, 1H), 7.22 (s, 1H), 4.05 (s, 2H), 3.77 (s, 3H), 3.36 (s, 3H), 2.35 (s, 3H), 2.28 (s, 3H) |
| II-a-13 | F | 3-Me | 6-F | Me | Me | Me | $^1$H-NMR(400 MHz, d6-DMSO, shift in ppm): 7.22 (m, 1H), 6.98 (t, 1H), 3.92 (s, 2H), 3.78 (s, 3H), 3.35 (s, 3H), 2.28 (s, 3H), 2.20 (s, 3H) |
| II-a-14 | Br | 4-Br | 6-OCF$_3$ | Me | Me | Me | $^1$H-NMR (400 MHz, d6-DMSO, shift in ppm): 7.99 (s, 1H), 7.68 (s, 1H), 4.09 (s, 2H), 3.77 (s, 3H), 3.35 (s, 3H), 2.28 (s, 3H) |
| II-a-15 | Cl | 3-Me | 6-F | Me | Me | Me | $^1$H-NMR(400 MHz, d6-DMSO, shift in ppm): 7.32 (m, 1H), 7.13 (t, 1H), 4.05 (s, 2H), 3.78 (s, 3H), 3.35 (s, 3H), 2.53 (s, 3H), 2.28 (s, 3H) |
| II-a-16 | F | 3-OMe | 6-F | Me | Me | Me | $^1$H-NMR(400 MHz, d6-DMSO, shift in ppm): 7.12 (m, 1H), 7.02 (t, 1H), 3.92 (s, 2H), 3.82 (s, 3H), 3.78 (s, 3H), 3.35 (s, 3H), 2.25 (s, 3H), |
| II-a-17 | Cl | 4-Br | 6-Cl | Me | Me | Me | $^1$H-NMR(400 MHz, d6-DMSO, shift in ppm): 7.79 (s, 2H), 4.15 (s, 2H), 3.79 (s, 3H), 3.35 (s, 3H), 2.28 (s, 3H) |
| II-a-18 | Cl | 6-Cl | H | Me | i-Bu | Et | $^1$H-NMR (400 MHz, CDCl$_3$, shift in ppm): 7.32 (d, 2H), 7.15 (m, 1H), 4.32 (m, 4H), 3.40 and 3.22 (in each case s, together 3H), 2.70 and 2.42 (in each case m, together 2H) 2.00 (m, 1H), 1.42 (m, 3H), 0.95 (m, 6H) |
| II-a-19 | I | H | H | Me | Me | Me | $^1$H-NMR(400 MHz, d6-DMSO, shift in ppm): 7.82 (d, 2H), 7.32 (m, 2H), 7.02 (t, 1H), 4.03 (s, 2H), 3.80 (s, 3H), 3.36 (s, 3H), 2.26 (s, 3H) |
| II-a-20 | Cl | 4-Cl | 6-Br | Me | Me | Me | $^1$H-NMR (400 MHz, d6-DMSO, shift in ppm): 7.82 (s, 1H), 7.72 (s, 1H), 4.21 (s, 2H), 3.79 (s, 3H), 3.38 (s, 3H), 2.28 (s, 3H) |
| II-a-21 | Cl | 6-CF$_3$ | H | Me | Me | Me | $^1$H-NMR (400 MHz, d6-DMSO, shift in ppm): 7.82 (d, 1H), 7.75 (d, 1H), 7.54 (t, 1H), 4.21 (s, 2H), 3.79 (s, 3H), 3.30 (s, 3H), 2.28 (s, 3H) |
| II-a-22 | 2-CF$_3$ | 5-CF$_3$ | H | Me | Me | Me | $^1$H-NMR (400 MHz, d6-DMSO, shift in ppm): 7.92 (t, 1H), 7.90 (s, 1H), 7.85 (d, 1H), 4.26 (s, 2H), 3.79 (s, 3H), 3.35 (s, 3H), 2.27 (s, 3H) |
| II-a-23 | Cl | 4-Cl | 6-c-Pr | Me | Me | Me | $^1$H-NMR (400 MHz, d6-DMSO, shift in ppm): 7.42 (s, 1H), 7.05 (s, 1H), 4.23 (s, 2H), 3.79 (s, 3H), 3.38 (s, 3H), 2.28 (s, 3H), 1.82 (m, 1H), 0.88 (m, 2H), 0.68 (m, 2H) |
| II-a-24 | Cl | 4-Cl | 6-Br | Me | Me | Me | $^1$H-NMR (400 MHz, d6-DMSO, shift in ppm): 7.81 (s, 1H), 7.71 (s, 1H), 4.22 (s, 2H), 3.78 (s, 3H), 3.38 (s, 3H), 2.28 (s, 3H) |

TABLE 26-continued

Compounds of the general formula (II)

(II)

$$\text{structure with substituents A, B, N-N, CO}_2R^9, \text{ aryl ring with X, Y, Z}$$

| No. | X | Y | Z | A | B | R⁹ | Analytical data |
|---|---|---|---|---|---|---|---|
| II-a-25 | Cl | 4-Br | 6-OCF₃ | Me | Me | Me | ¹H-NMR (400 MHz, d6-DMSO, shift in ppm): 7.88 (s, 1H), 7.68 (s, 1H), 4.08 (s, 2H), 3.78 (s, 3H), 3.33 (s, 3H), 2.28 (s, 3H) |
| II-a-26 | Br | 4-Cl | 6-OCF₃ | Me | Me | Me | ¹H-NMR (400 MHz, d6-DMSO, shift in ppm): 7.92 (s, 1H), 7.61 (s, 1H), 4.11 (s, 2H), 3.78 (s, 3H), 3.35 (s, 3H), 2.28 (s, 3H) |
| II-a-27 | Cl | 4-Br | 6-OCF₃ | Me | Me | Me | ¹H-NMR (400 MHz, d6-DMSO, shift in ppm): 8.18 (s, 1H), 7.93 (s, 1H), 4.18 (s, 2H), 3.78 (s, 3H), 3.32 (s, 3H), 2.28 (s, 3H) |

B. Formulation Examples a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
   75 parts by weight of a compound of the formula (I) and/or a salt thereof,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill, and granulating the powder in a fluidized bed by spraying on water as granulating liquid.

f) Water-dispersible granules are also obtained by homogenizing and precomminuting
   25 parts by weight of a compound of the formula (I),
   5 parts by weight of sodium 2,2'-dinaphthylmethane-6,6'-disulfonate,
   2 parts by weight of sodium oleoylmethyltaurate,
   1 parts by weight of polyvinyl alcohol,
   17 parts by weight of calcium carbonate and
   50 parts by weight of water
   in a colloid mill, then grinding the mixture in a bead mill, and atomizing and drying the resulting suspension in a spray tower, using a single-fluid nozzle.

C. Biological Examples

1. Herbicidal Pre-Emergence Effect Against Harmful Plants

Seeds of monocotyledonous or dicotyledonous weeds or crop plants are placed in sandy loam soil in wood-fiber pots and covered with soil. The compounds according to the invention, formulated in the form of wettable powders (WP) or emulsion concentrates (EC), are then applied to the surface of the soil cover in the form of an aqueous suspension or emulsion at a water application rate of 600 to 800 l/ha (converted), with addition of 0.2% wetting agent. After the treatment, the pots are placed in the greenhouse and kept under good growth conditions for the test plants. The damage to the test plants is scored visually in comparison with untreated controls after an experimental time of 3 weeks has elapsed (herbicidal activity in percent (%): 100% activity=plants have died, 0% activity=like control plants). Here, for example, the compounds Nos. I-1-c-8, I-1-a-16 and I-1-c-13 show, at an application rate of 320 g/ha, each at least 90% activity against *Matricaria inodora*, *Stellaria media* and *Veronica persica*.

2. Herbicidal Post-Emergence Activity Against Harmful Plants

Seeds of monocotyledonous or dicotyledonous weeds or crop plants are placed in sandy loam soil in wood-fiber pots, covered with soil and grown in the greenhouse under good growth conditions. 2 to 3 weeks after sowing, the test plants are treated in the one-leaf stage. The compounds according to the invention, formulated in the form of wettable powders (WP) or emulsion concentrates (EC), are then sprayed onto the green plant parts in the form of an aqueous suspension or emulsion at a water application rate of 600 to 800 l/ha (converted), with addition of 0.2% wetter. After the test plants have been left to stand under optimal growth conditions in the greenhouse for approximately 3 weeks, the activity of the preparations is scored visually in comparison with untreated controls (herbicidal activity in percent (%): 100% activity=plants have died, 0% activity=like control plants). Here, for example the compounds I-1-a-27, I-1-c-7, I-1-c-8, I-1-b-3, I-1-b-1, I-1-c-9, I-1-a-9, I-1-c-14, I-1-g-1 and I-1-a-25 show, at an application rate of 320 g/ha, at least 80% activity against *Amaranthus retroflexus, Veronica persica* and *Viola tricolor*.

3. Insecticidal Activity

Example A

Myzus Test (MYZUPE Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration. Discs of Chinese cabbage (*Brassica pekinensis*) which are infested by all stages of the green peach aphid (*Myzus persicae*) are sprayed with an active compound preparation of the desired concentration. After the desired period of time, the effect in % is determined. 100% means that all aphids have been killed; 0% means that none of the aphids have been killed. In this test, for example, the compounds Nos. I-1-a-4 and I-1-a-8 show, at an application rate of 500 g/ha, at least 80% activity.

Example B

*Heliothis Virescens* Test (Spray Treatment)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration. Soybean leaves (*Glycine max.*) are sprayed with an active compound preparation of the desired concentration and, after drying, populated with eggs of the tobacco bud worm (*Heliothis virescens*). After 7 days, the effect in % is determined. 100% means that all the eggs have been killed; 0% means that none of the eggs have been killed. In this test, for example, the compound No. I-1-a-5 shows, at an application rate of 500 g/ha, at least 80% activity.

Example C

*Meloidogyne Incognita* Test (MELGIN)

| Solvents: | 78.0 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with water to the desired concentration. Containers are filled with sand, solution of active compound, *Meloidogyne incognita* egg/larvae suspension and lettuce seeds. The lettuce seeds germinate and the plants develop. On the roots, galls are formed. After the desired period of time, the nematicidal activity is determined in % by the formation of galls. 100% means that no galls are formed; 0% means that the number of galls on the treated plants corresponds to that of the untreated control. In this test, for example, the compound No. I-1-a-10 shows, at an application rate of 20 ppm, an efficacy of at least 80%.

The invention claimed is:
1. A 4-phenylpyridazinone of formula (I) or a salt thereof

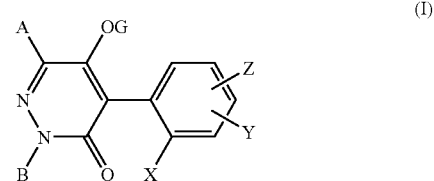

in which
A and B are in each case independently of one another hydrogen or $(C_1-C_6)$-alkyl;
G is hydrogen, $C(=O)R^1$, $C(=L)MR^2$, $SO_2R^3$, $P(=L)R^4R^5$, $C(=L)NR^6R^7$ or E;
E is a metal ion equivalent or an ammonium ion;
L is oxygen or sulfur;
M is oxygen or sulfur;
$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, each of which is substituted by n halogen atoms, a fully saturated 3- to 6-membered ring comprising 3 to 5 carbon atoms and 1 to 3 heteroatoms selected from the group consisting of oxygen, sulfur and nitrogen which is substituted by n radicals from the group consisting of halogen, $(C_1-C_4)$-alkyl and $(C_1-C_4)$-alkoxy, $(C_3-C_6)$-cycloalkyl, phenyl, phenyl-$(C_1-C_4)$-alkyl, heteroaryl, phenoxy-$(C_1-C_4)$-alkyl or heteroaryloxy-$(C_1-C_4)$-alkyl substituted by n radicals selected from the group consisting of halogen, $(C_1-C_4)$-alkyl and $(C_1-C_4)$-alkoxy;
$R^2$ is $(C_1-C_6)$-alkyl, $(C_2-C_6)$-alkenyl, $(C_1-C_4)$-alkoxy-$(C_1-C_6)$-alkyl or di-$(C_1-C_4)$-alkoxy-$(C_1-C_6)$-alkyl, each of which is substituted by n halogen atoms,
or is $(C_3-C_6)$-cycloalkyl, phenyl or benzyl, each of which is substituted by n radicals selected from the group consisting of halogen, $(C_1-C_4)$-alkyl and $(C_1-C_4)$-alkoxy;

$R^3$, $R^4$ and $R^5$ are each independently of one another ($C_1$-$C_6$)-alkyl which is substituted by n halogen atoms, ($C_1$-$C_4$)-alkoxy, N—($C_1$-$C_6$)-alkylamino, N,N-di-($C_1$-$C_6$)-alkylamino, ($C_1$-$C_4$)-alkylthio, ($C_2$-$C_4$)-alkenyl or ($C_3$-$C_6$)-cycloalkylthio, or phenyl, benzyl, phenoxy or phenylthio which is substituted by n radicals selected from the group consisting of halogen, ($C_1$-$C_4$)-alkyl and ($C_1$-$C_4$)-alkoxy;

$R^6$ and $R^7$ are each independently of one another hydrogen, ($C_1$-$C_6$)-alkyl which is substituted by n halogen atoms, ($C_3$-$C_6$)-cycloalkyl, ($C_2$-$C_6$)-alkenyl, ($C_1$-$C_6$)-alkoxy or ($C_1$-$C_4$)-alkoxy-($C_1$-$C_6$)-alkyl, phenyl or benzyl, each of which is substituted by n radicals selected from the group consisting of halogen, ($C_1$-$C_4$)-alkyl and ($C_1$-$C_4$)-alkoxy;

or $R^6$ and $R^7$ together with the nitrogen atom to which they are attached form a 3- to 6-membered ring which contains 2 to 5 carbon atoms and 0 or 1 oxygen or sulfur atoms;

m is 1, 2 or 3;

n is 0, 1, 2 or 3;

X is halogen, cyano, ($C_3$-$C_6$)-cycloalkyl, nitro or is ($C_1$-$C_6$)-alkyl or ($C_1$-$C_6$)-alkoxy, each of which is substituted by m halogen atoms or phenyl substituted by n halogen atoms;

Y and Z are each independently of one another hydrogen, halogen, cyano, nitro, ($C_3$-$C_6$)-cycloalkyl or are ($C_1$-$C_6$)-alkyl, ($C_1$-$C_6$)-alkoxy or phenyl, each of which is substituted by n halogen atoms, with the proviso that neither Y nor Z is a ($C_1$-$C_6$)-alkyl or ($C_1$-$C_6$)-alkoxy radical located in position 6 if n is 0;

with the proviso that the compound is not:

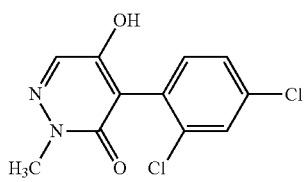

4(2,4-dichlorophenyl)-5-hydroxy-2-methylpyridazin-3(2H)-one.

2. The 4-phenylpyridazinone as claimed in claim 1 in which

A is hydrogen or ($C_1$-$C_6$)-alkyl;

B is hydrogen or ($C_1$-$C_6$)-alkyl;

G is hydrogen, C(=O)$R^1$, C(=L)M$R^2$, SO$_2R^3$, P(=L)$R^4R^5$, C(=L)N$R^6R^7$, or E;

E is Na$^+$, K$^+$, (Mg$^{2+}$)$_{1/2}$, (Ca$^{2+}$)$_{1/2}$, $R^{13}R^{14}R^{15}R^{16}$N$^+$ or NH$_4^+$;

$R^{13}$, $R^{14}$, $R^{15}$ and $R^{16}$ are independently of one another ($C_1$-$C_6$)-alkyl or benzyl;

L is oxygen;

M is oxygen;

$R^1$ is ($C_1$-$C_6$)-alkyl which is substituted by n halogen atoms or is ($C_3$-$C_6$)-cycloalkyl, phenyl or phenyl-($C_1$-$C_4$)-alkyl, each of which is substituted by n radicals selected from the group consisting of halogen, ($C_1$-$C_4$)-alkyl and ($C_1$-$C_4$)-alkoxy;

$R^2$ is ($C_1$-$C_6$)-alkyl which is substituted by n halogen atoms or is ($C_3$-$C_6$)-cycloalkyl, phenyl or benzyl, each of which is substituted by n radicals selected from the group consisting of halogen, ($C_1$-$C_4$)-alkyl and ($C_1$-$C_4$)-alkoxy;

$R^3$, $R^4$ and $R^5$ are each independently of one another ($C_1$-$C_6$)-alkyl which is substituted by n halogen atoms or are phenyl or benzyl which are substituted by n radicals selected from the group consisting of halogen, ($C_1$-$C_4$)-alkyl and ($C_1$-$C_4$)-alkoxy;

$R^6$ and $R^7$ are each independently of one another hydrogen, ($C_1$-$C_6$)-alkyl which is substituted by n halogen atoms or phenyl or benzyl which are substituted by n radicals selected from the group consisting of halogen, ($C_1$-$C_4$)-alkyl and ($C_1$-$C_4$)-alkoxy;

m is 1, 2 or 3;

n is 0, 1, 2, or 3;

X is halogen, cyano, ($C_3$-$C_6$)-cycloalkyl, nitro or is ($C_1$-$C_6$)-alkyl or ($C_1$-$C_6$)-alkoxy, each of which is substituted by m halogen atoms;

Y and Z are each independently of one another hydrogen, halogen, cyano, nitro, ($C_3$-$C_6$)-cycloalkyl or are ($C_1$-$C_6$)-alkyl, ($C_1$-$C_6$)-alkoxy or phenyl, each of which is substituted by n halogen atoms, with the proviso that neither Y nor Z is a ($C_1$-$C_6$)-alkyl or ($C_1$-$C_6$)-alkoxy radical located in position 6 if n is 0.

3. The 4-phenylpyridazinone as claimed in claim 1 in which

A is hydrogen, methyl, ethyl, or isobutyl;

B is hydrogen, methyl, ethyl, isobutyl, or tert-butyl;

G is hydrogen, C(=O)$R^1$, C(=L)M$R^2$, SO$_2R^3$, P(=L)$R^4R^5$, C(=L)N$R^6R^7$ or E;

E is Na$^+$, K$^+$, (Mg$^{2+}$)$_{1/2}$, (Ca$^{2+}$)$_{1/2}$, (CH$_3$)$_4$N$^+$ or NH$_4^+$;

L is oxygen;

M is oxygen;

$R^1$ is ($C_1$-$C_6$)-alkyl or ($C_3$-$C_6$)-cycloalkyl;

$R^2$ is ($C_1$-$C_6$)-alkyl, ($C_3$-$C_6$)-cycloalkyl or benzyl;

$R^3$, $R^4$ and $R^5$ are each independently of one another ($C_1$-$C_6$)-alkyl, phenyl or benzyl;

$R^6$ and $R^7$ are each independently of one another hydrogen, ($C_1$-$C_6$)-alkyl, phenyl or benzyl;

m is 1, 2 or 3;

n is 0, 1, 2 or 3;

and

X is fluorine, bromine, chlorine, iodine, cyano, nitro, trifluoromethyl, trifluoromethoxy or cyclopropyl;

Y is hydrogen, fluorine, bromine, chlorine, iodine, methyl, ethyl, methoxy, ethoxy, trifluoromethyl, trifluoromethoxy or cyclopropyl;

Z is hydrogen, fluorine, bromine, chlorine, iodine, methyl, ethyl, methoxy, ethoxy, trifluoromethyl, trifluoromethoxy, cyclopropyl, chlorophenyl or fluorophenyl, with the proviso that neither Y nor Z is a radical selected from the group consisting of methyl, ethyl, methoxy and ethoxy located in position 6 if n is 0.

4. A herbicidal composition which comprises an effective amount of at least one 4-phenylpyridazinone of the formula (I) as claimed in claim 1.

5. The herbicidal composition as claimed in claim 4 as a mixture with at least one formulation auxiliary.

6. The herbicidal composition as claimed in claim 4 which comprises at least one further pesticidally active compound selected from the group consisting of insecticides, acaricides, herbicides, fungicides, safeners and growth regulators.

7. The herbicidal composition as claimed in claim 4 which comprises a safener.

8. The herbicidal composition as claimed in claim 4 which comprises a further herbicide.

9. A method for controlling unwanted plants comprising applying an effective amount of at least one 4-phenylpyridazinone of formula (I) as claimed in claim 1 to plants or to a site where an unwanted plant is growing.

10. A 4-phenylpyridazinone of formula (I) as claimed in claim 1 which is capable of controlling unwanted plants.

11. A 4-phenylpyridazinone as claimed in claim 10 which is capable of controlling unwanted plants in crops of useful plants.

12. The 4-phenylpyridazinone as claimed in claim 11 wherein the useful plants are transgenic useful plants.

13. A 4-phenylpyridazinone of formula (I) as claimed in claim 1 capable of use as an insecticide.

14. A 4-phenylpyridazinone of formula (I) or a salt thereof

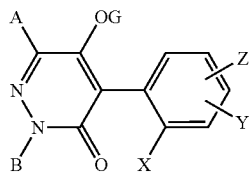

(I)

in which
A is $(C_1-C_6)$-alkyl;
B is hydrogen or $(C_1-C_6)$-alkyl;
G is hydrogen, $C(=O)R^1$, $C(=L)MR^2$, $SO_2R^3$, $P(=L)R^4R^5$, $C(=L)NR^6R^7$ or E;
E is a metal ion equivalent or an ammonium ion;
L is oxygen or sulfur;
M is oxygen or sulfur;
$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, each of which is substituted by n halogen atoms, a fully saturated 3- to 6-membered ring comprising 3 to 5 carbon atoms and 1 to 3 heteroatoms selected from the group consisting of oxygen, sulfur and nitrogen which is substituted by n radicals from the group consisting of halogen, $(C_1-C_4)$-alkyl and $(C_1-C_4)$-alkoxy, $(C_3-C_6)$-cycloalkyl, phenyl, phenyl-$(C_1-C_4)$-alkyl, heteroaryl, phenoxy-$(C_1-C_4)$-alkyl or heteroaryloxy-$(C_1-C_4)$-alkyl substituted by n radicals selected from the group consisting of halogen, $(C_1-C_4)$-alkyl and $(C_1-C_4)$-alkoxy;
$R^2$ is $(C_1-C_6)$-alkyl, $(C_2-C_6)$-alkenyl, $(C_1-C_4)$-alkoxy-$(C_1-C_6)$-alkyl or di-$(C_1-C_4)$-alkoxy-$(C_1-C_6)$-alkyl, each of which is substituted by n halogen atoms,
or is $(C_3-C_6)$-cycloalkyl, phenyl or benzyl, each of which is substituted by n radicals selected from the group consisting of halogen, $(C_1-C_4)$-alkyl and $(C_1-C_4)$-alkoxy;
$R^3$, $R^4$ and $R^5$ are each independently of one another $(C_1-C_6)$-alkyl which is substituted by n halogen atoms, $(C_1-C_4)$-alkoxy, N—$(C_1-C_6)$-alkylamino, N,N-di-$(C_1-C_6)$-alkylamino, $(C_1-C_4)$-alkylthio, $(C_2-C_4)$-alkenyl or $(C_3-C_6)$-cycloalkylthio,
or phenyl, benzyl, phenoxy or phenylthio which is substituted by n radicals selected from the group consisting of halogen, $(C_1-C_4)$-alkyl and $(C_1-C_4)$-alkoxy;
$R^6$ and $R^7$ are each independently of one another hydrogen, $(C_1-C_6)$-alkyl which is substituted by n halogen atoms, $(C_3-C_6)$-cycloalkyl, $(C_2-C_6)$-alkenyl, $(C_1-C_6)$-alkoxy or $(C_1-C_4)$-alkoxy-$(C_1-C_6)$-alkyl,
phenyl or benzyl, each of which is substituted by n radicals selected from the group consisting of halogen, $(C_1-C_4)$-alkyl and $(C_1-C_4)$-alkoxy;
or $R^6$ and $R^7$ together with the nitrogen atom to which they are attached form a 3- to 6-membered ring which contains 2 to 5 carbon atoms and 0 or 1 oxygen or sulfur atoms;
m is 1, 2 or 3;
n is 0, 1, 2 or 3;
X is halogen, cyano, $(C_3-C_6)$-cycloalkyl, nitro or is $(C_1-C_6)$-alkyl or $(C_1-C_6)$-alkoxy, each of which is substituted by m halogen atoms or phenyl substituted by n halogen atoms;
Y and Z are each independently of one another hydrogen, halogen, cyano, nitro, $(C_3-C_6)$-cycloalkyl or are $(C_1-C_6)$-alkyl, $(C_1-C_6)$-alkoxy or phenyl, each of which is substituted by n halogen atoms,
with the proviso that neither Y nor Z is a $(C_1-C_6)$-alkyl or $(C_1-C_6)$-alkoxy radical located in position 6 if n is 0.

15. A 4-phenylpyridazinone of formula (I) or a salt thereof

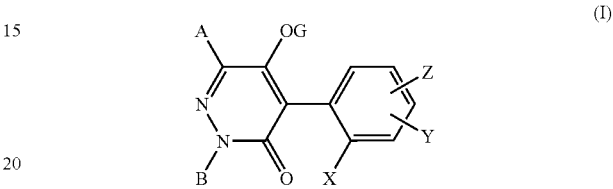

(I)

in which
A is hydrogen or $(C_1-C_6)$-alkyl;
B is hydrogen or $(C_2-C_6)$-alkyl;
G is hydrogen, $C(=O)R^1$, $C(=L)MR^2$, $SO_2R^3$, $P(=L)R^4R^5$, $C(=L)NR^6R^7$ or E;
E is a metal ion equivalent or an ammonium ion;
L is oxygen or sulfur;
M is oxygen or sulfur;
$R^1$ is $(C_1-C_6)$-alkyl, $(C_2-C_6)$-alkenyl, $(C_1-C_4)$-alkoxy-$(C_1-C_6)$-alkyl, di-$(C_1-C_4)$-alkoxy-$(C_1-C_6)$-alkyl or $(C_1-C_4)$-alkylthio-$(C_1-C_6)$-alkyl, each of which is substituted by n halogen atoms, a fully saturated 3- to 6-membered ring comprising 3 to 5 carbon atoms and 1 to 3 heteroatoms selected from the group consisting of oxygen, sulfur and nitrogen which is substituted by n radicals from the group consisting of halogen, $(C_1-C_4)$-alkyl and $(C_1-C_4)$-alkoxy, $(C_3-C_6)$-cycloalkyl, phenyl, phenyl-$(C_1-C_4)$-alkyl, heteroaryl, phenoxy-$(C_1-C_4)$-alkyl or heteroaryloxy-$(C_1-C_4)$-alkyl substituted by n radicals selected from the group consisting of halogen, $(C_1-C_4)$-alkyl and $(C_1-C_4)$-alkoxy;
$R^2$ is $(C_1-C_6)$-alkyl, $(C_2-C_6)$-alkenyl, $(C_1-C_4)$-alkoxy-$(C_1-C_6)$-alkyl or di-$(C_1-C_4)$-alkoxy-$(C_1-C_6)$-alkyl, each of which is substituted by n halogen atoms,
or is $(C_3-C_6)$-cycloalkyl, phenyl or benzyl, each of which is substituted by n radicals selected from the group consisting of halogen, $(C_1-C_4)$-alkyl and $(C_1-C_4)$-alkoxy;
$R^3$, $R^4$ and $R^5$ are each independently of one another $(C_1-C_6)$-alkyl which is substituted by n halogen atoms, $(C_1-C_4)$-alkoxy, N—$(C_1-C_6)$-alkylamino, N,N-di-$(C_1-C_6)$-alkylamino, $(C_1-C_4)$-alkylthio, $(C_2-C_4)$-alkenyl or $(C_3-C_6)$-cycloalkylthio,
or phenyl, benzyl, phenoxy or phenylthio which is substituted by n radicals selected from the group consisting of halogen, $(C_1-C_4)$-alkyl and $(C_1-C_4)$-alkoxy;
$R^6$ and $R^7$ are each independently of one another hydrogen, $(C_1-C_6)$-alkyl which is substituted by n halogen atoms, $(C_3-C_6)$-cycloalkyl, $(C_2-C_6)$-alkenyl, $(C_1-C_6)$-alkoxy or $(C_1-C_4)$-alkoxy-$(C_1-C_6)$-alkyl,
phenyl or benzyl, each of which is substituted by n radicals selected from the group consisting of halogen, $(C_1-C_4)$-alkyl and $(C_1-C_4)$-alkoxy;
or $R^6$ and $R^7$ together with the nitrogen atom to which they are attached form a 3- to 6-membered ring which contains 2 to 5 carbon atoms and 0 or 1 oxygen or sulfur atoms;

m is 1, 2 or 3;
n is 0, 1, 2 or 3;
X is halogen, cyano, $(C_3-C_6)$-cycloalkyl, nitro or is $(C_1-C_6)$-alkyl or $(C_1-C_6)$-alkoxy, each of which is substituted by m halogen atoms or phenyl substituted by n halogen atoms;
Y and Z are each independently of one another hydrogen, halogen, cyano, nitro, $(C_3-C_6)$-cycloalkyl or are $(C_1-C_6)$-alkyl, $(C_1-C_6)$-alkoxy or phenyl, each of which is substituted by n halogen atoms, with the proviso that neither Y nor Z is a $(C_1-C_6)$-alkyl or $(C_1-C_6)$-alkoxy radical located in position 6 if n is 0.

* * * * *